(12) United States Patent
Wands

(10) Patent No.: US 10,813,984 B2
(45) Date of Patent: Oct. 27, 2020

(54) ASPARTATE-β-HYDROXYLASE INDUCES EPITOPE-SPECIFIC T CELL RESPONSES IN TUMORS

(71) Applicant: Rhode Island Hospital, Providence, RI (US)

(72) Inventor: Jack R. Wands, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 14/696,207

(22) Filed: Apr. 24, 2015

(65) Prior Publication Data

US 2015/0306198 A1     Oct. 29, 2015

Related U.S. Application Data

(60) Provisional application No. 61/983,874, filed on Apr. 24, 2014.

(51) Int. Cl.
| | | |
|---|---|---|
| *A61K 39/00* | (2006.01) | |
| *C12N 9/02* | (2006.01) | |
| *A61B 17/12* | (2006.01) | |

(52) U.S. Cl.
CPC .... *A61K 39/0011* (2013.01); *A61B 17/12186* (2013.01); *C12N 9/0071* (2013.01); *C12Y 114/11016* (2013.01); *A61K 2039/5154* (2013.01); *A61K 2039/5158* (2013.01); *A61K 2039/57* (2013.01); *A61K 2039/572* (2013.01); *A61K 2039/585* (2013.01)

(58) Field of Classification Search
None
See application file for complete search history.

(56) References Cited

U.S. PATENT DOCUMENTS

| | | | | |
|---|---|---|---|---|
| 6,783,758 B2 | 8/2004 | Wands et al. | | |
| 6,797,696 B2* | 9/2004 | Wands | ................. | A61K 31/00 424/94.1 |
| 6,812,206 B2* | 11/2004 | Wands | ................. | A61K 31/00 424/141.1 |
| 2002/0110559 A1* | 8/2002 | Wands | ................. | A61K 31/00 424/146.1 |
| 2005/0123545 A1* | 6/2005 | Wands | ................. | A61K 31/00 424/146.1 |
| 2011/0076290 A1 | 3/2011 | Shimoda et al. | | |
| 2011/0229504 A1 | 9/2011 | Fritsche et al. | | |
| 2013/0330335 A1 | 12/2013 | Robert et al. | | |
| 2014/0271691 A1* | 9/2014 | Biswas | ............. | A61K 39/0011 424/185.1 |
| 2016/0250307 A1* | 9/2016 | Weinschenk | ....... | A61K 39/0011 424/185.1 |

FOREIGN PATENT DOCUMENTS

| | | |
|---|---|---|
| CN | 103789280 A | 5/2014 |
| EP | 0 10 9942 A2 | 5/1984 |
| JP | 2008-527001 A | 7/2008 |
| JP | 2013-500261 A | 1/2013 |
| WO | WO-2005016281 A2 | 2/2005 |
| WO | 2006/076678 A2 | 7/2006 |
| WO | 2011/011688 A2 | 1/2011 |
| WO | 2013/106834 A2 | 7/2013 |
| WO | 2014/010231 A1 | 1/2014 |

OTHER PUBLICATIONS

Shibagaki, N. et al., The Journal of Immunology, 168: 2393-2401, 2002.*
Mizukoshi, E., et al., International Journal of Cancer, 126: 2164-2174, 2010; online Sep. 8, 2009.*
Wu, Y., et al. Int. J. Cancer, 98: 748-753, 2002.*
Brinkman, J. A., et al., Expert Opinion Biol. Ther., 4(2): 181-198, 2004.*
Meleif, C.J.M. and Kast, M., Immunological Reviews, 146: 167-177, 1995.*
Ayaru, Lakshmana et al., "Unmasking of alpha-Fetoprotein-Specific CD4+ T Cell Responses in hepatocellular Carcinoma Patients Undergoing Embolization," The Journal of Immunology, vol. 178:1914-1922 (2007).
Breous, Ekaterina et al., "Potential of immunotherapy for hepatocellular carcinoma," Journal of Hepatlogy, vol. 54:830-834 (2011).
Chen, Mei-Ling et al., "Sorafenib relieves cell-intrinsic and cell-extrinsic inhibitions of effector T cells in tumor microenvironment to augment antitumor immunity," International Journal of Cancer, vol. 134:319-331 (2014).
Dannull, Jens et al., "Enhancement of vaccine-mediated antitumor immunity in cancer patients after depletion of regulatory T cells," The Journal of Clinical Investigation, vol. 115(12):3623-3633 (2005).
De Groot, Anne S. et al., "An Interactive Web Site Providing Major Histocompatibility Ligand Predictions: Application to HIV Research," AIDS Research and Human Retroviruses, vol. 13(7):529-531 (1997).
De Groot, Anne S. et al., "Engineering immunogenic consensus T helper epitopes for a cross-clade HIV vaccine," Methods, vol. 34:476-487 (2004).
De La Monte, Suzanne M. et al., "Aspartyl-(asparaginyl)-beta-hydroxylase regulates hepatocellular carcinoma invasiveness," Journal of Hepatology, vol. 44:971-983 (2006).
El-Serag, Hashem B. et al., "Hepatocellular Carcinoma: Epidemiology and Molecular Carcinogenesis," Gastroenterology, vol. 132:2557-2576 (2007).
Fong, Yuman et al., "An Analysis of 412 Cases of Hepatocellular Carcinoma at a Western Center," Annals of Surgery, vol. 229(6):790-800 (1999).
Frentsch, Marco et al., "Direct access to CD4+ T cells specific for defined antigens according to CD154 expression," Nature Medicine, vol. 11(10):1118-1124 (2005).
Gronke, Robert S. et al., "Aspartyl beta-hydroxylase: In vitro hydroxylation of a synthetic peptide based on the structure of the first growth factor-like domain of human factor IX," Proc. Natl. Acad. Sci. USA, vol. 86:3609-3613 (1989).

(Continued)

*Primary Examiner* — Peter J Reddig
(74) *Attorney, Agent, or Firm* — Mintz Levin Cohn Ferris Glovsky and Popeo, P.C.; Ingrid A. Beattie

(57) ABSTRACT

The present invention provides a peptide-based immunotherapy for ASPH-expressing tumors.

16 Claims, 8 Drawing Sheets
Specification includes a Sequence Listing.

(56) References Cited

OTHER PUBLICATIONS

Gronke, Robert S. et al., "Partial Purification and Characterization of Bovine Liver Aspartyl beta-Hydroxylase," The Journal of Biological Chemistry, vol. 265(15):8558-8565 (1990).
Hoechst, Bastian et al., "A New Population of Myeloid-Derived Suppressor Cells in Hepatocellular Carcinoma Patients Induces CD4+CD2+Foxp3+ T Cells," Gastroenterology, vol. 135:234-243 (2008).
Jia, Steve et al., "cDNA Cloning and Expression of Bovine Aspartyl (Asparaginyl) beta-Hydroxylase," The Journal of Biological Chemistry, vol. 267(20):14322-14327 (1992).
Kennedy, Richard et al., "Multiple roles for CD4+ T cells in anti-tumor immune responses," Immunological Reviews, vol. 222:129-144 (2008).
Komori, Hiroyuki et al., "Identification of HLA-A2- or HLA-A24- Restricted CTL Epitopes Possibly Useful for Glypican-3-Specific Immunotherapy of Hepatocelullar Carcinoma," Clin. Cancer Res., vol. 12(9):2689-2697 (2006).
Lavaissiere, Laurent et al., "Overexpression of Human Aspartyl(Asparaginyl)beta-Hydroxylase in Hepatocellular Carcinoma and Cholangiocarcinoma," J. Clin. Invest., vol. 98(6):1313-1323 (1996).
Liu, Yang et al., "Hierarchy of alpha Fetoprotein (AFP)-Specific T Cell Responses in Subjects with AFP-Positive Hepatocellular Cancer," J. Immunol., vol. 177(1):712-721 (2006).
Lutsiak, M.E. Christine et al., "Inhibition of CD4+25+ T regulatory cell function implicated in enhanced immune response by low-dose cyclophosphamide," Blood, vol. 105(7):2862-2868 (2005).
Marzo, Amanda L. et al., "Tumor-Specific CD4+ T Cells Have a Major 'Post-Licensing' Role in CTL Mediated Anti-Tumor Immunity," The Journal of Immunology, vol. 165:6047-6055 (2000).
Meyer, T.P.H. et al., "Filter Buffy Coats (FBC): A source of peripheral blood leukocytes recovered from leukocyte depletion filters," Journal of Immunological Methods, vol. 307:150-166 (2005).
Mishra, Sasmita et al., "Peptide-pulsed dendritic cells induce the hepatitis C viral epitope-specific responses of naive human T cells," Vaccine, vol. 32:3285-3292 (2014).
Moser, Janice M. et al., "Optimization of a dendritic cell-based assay for the in vitro priming of naive human CD4+ T cells," Journal of Immunological Methods, vol. 353:8-19 (2010).
Nobuoka, Daisuke et al., "Radiofrequency ablation for hepatocellular carcinoma induces glypican-3 peptide-specific cytotoxic T lymphocytes," International Journal of Oncology, vol. 40:63-70 (2012).
Noda, Takehiro et al., "Immunization with ASPH-loaded dendritic cells produces anti-tumor effects in a rat model of intrahepatic cholangiocarcinoma," Hepatology, vol. 55(1):86-97 (2012).
Sakaguchi, Shimon, "Naturally Arising CD4+ Regulatory T Cells for Immunologic Self-Tolerance and Negative Control of Immune Responses," Annu. Rev. Immunol., vol. 22:531-562 (2004).
Schafer, James Robert A. et al., "Prediction of well-conserved HIV-1 ligands using a matrix-based algorithm, EpiMatrix," Vaccine, vol. 16(19):1880-1884 (1998).
Schiavoni, Giovanna et al., "Cyclophosphamide induces type I Interferon and augments the number of CD44hi T lymphocytes in mice: implications for strategies of chemoimmunotherapy of cancer," Blood, vol. 95:2024-2030 (2000).

Schutte, Kerstin et al., "Hepatocellular Carcinoma—Epidemiological Trends and Risk Factors," Digestive Diseases, vol. 27:80-92 (2009).
Sette, Alessandro et al., "Nine major HLA class I supertypes account for the vast preponderance of HLA-A and -B polymorphism," Immunogenetics, vol. 50:201-212 (1999).
Shang, Xiao-Ying et al., "The Spontaneous CD8+ T-Cell Response to HLA-A2-Restricted NY-ESO-1b Peptide in Hepatocellular Carcinoma Patients," Clinical Cancer Research, vol. 10:6946-6955 (2004).
Shi, Feng et al., "PD-1 and PD-L1 upregulation promotes CD8+ T-cell apoptosis and postoperative recurrence in hepatocellular carcinoma patients," International Journal of Cancer, vol. 128:887-896 (2011).
Shimoda, Masafumi et al., "Tumor progression-related transmembrane protein aspartate beta-hydroxylase is a target for immunotherapy of hepatocellular carcinoma," J. Hepatol., vol. 56(5):1129-1135 (2012).
Southwood, Scott et al., "Several Common HLA-DR Types Share Largely Overlapping Peptide Binding Repertoires," The Journal of Immunology, vol. 160:3363-3373 (1998).
Thimme, Robert et al., "Comprehensive Analysis of the alpha-Fetoprotein-Specific CD8+ T Cell Responses in Patients with Hepatocellular Carcinoma," Hepatology, vol. 48:1821-1833 (2008).
Wang, Kui et al., "Overexpression of Aspartyl-(Asparaginyl)-beta-Hydroxylase in Hepatocellular Carcinoma is Associated With Worse Surgical Outcome," Hepatology, vol. 52:164-173 (2010).
Wolfl, Matthias et al., "Activation-induced expression of CD137 permits detection, isolation, and expansion of the full repertoire of CD8+ T cells responding to antigen without requiring knowledge of epitope specificities," Blood, vol. 110(1):201-210 (2007).
Zhu, Andrew X., "Systemic Therapy of Advanced Hepatocellular Carcinoma: How Hopeful Should We Be?" The Oncologist, vol. 11:790-800 (2006).
Zitvogel, Laurence et al., "Immunological aspects of cancer chemotherapy," Nature Reviews Immunology, vol. 8:59-73 (2008).
Zou, Weiping et al., "Regulatory T cells, tumour immunity and immunotherapy," Nature Reviews Immunology, vol. 6:295-307 (2006).
Dinchuk et al., Aspartyl beta-hydroxylase (Asph) and an evolutionarily conserved isoform of Asph missing the catalytic domain share exons with junctin. J Biol Chem. Dec. 15, 2000;275(50):39543-54. GenBank Accession No. S83325.1.
Liu et al., Abrogation of local cancer recurrence after radiofrequency ablation by dendritic cell-based hyperthermic tumor vaccine. Mol Ther. Dec. 2009;17(12):2049-57.
Tomimaru Y, et al. Aspartate-β-hydroxylase Induces Epitope-specific T Cell Responses in Hepatocellular Carcinoma. Vaccine. 2015;33(10):1256-1266.
GenBank NCBI Accession No. S83325; 1 page Accessible on the Internet at URL: https://www.ncbi.nlm.nih.gov/nuccore/S83325.
International Search Report corresponding to International Patent Application No. PCT/US2015/027651, dated Oct. 28, 2015, 12 pages.
Parker et al. (Jan. 1, 1994) "Scheme for Ranking Potential HLA-A2 Binding Peptides Based on Independent Binding of Individual Peptide Side-Chains.", The Journal of Immunology, 152(1):163-175.

* cited by examiner

ASPARTATE-β-HYDROXYLASE INDUCES EPITOPE-SPECIFIC T CELL RESPONSES IN TUMORS

CROSS-REFERENCE TO RELATED APPLICATION

This application which claims priority to U.S. Provisional Application No. 61/983,874, filed on Apr. 24, 2014, the contents of all of which are incorporated herein by reference in its entirety.

INCORPORATION-BY-REFERENCE

The contents of the ASCII text file named "21486_621_SequenceListing_ST25.txt", which was created on Apr. 24, 2015 and is 18.7 KB (19,196 bytes) in size, are hereby incorporated by reference in their entireties.

STATEMENT AS TO FEDERALLY SPONSORED RESEARCH

This invention was made with U.S. government support under NIH grants CA-123544 and U19AI082642. The government has certain rights in the invention.

FIELD OF THE INVENTION

The present invention relates to a peptide based immunotherapy for cancers.

BACKGROUND OF THE INVENTION

Hepatocellular carcinoma (HCC), the third most common cause of cancer-related death worldwide, is characterized by a very poor prognosis and a high rate of mortality.[1,2] Available therapeutic modalities are largely inadequate. Currently, surgical resection is considered the optimal treatment approach. Only a small proportion of patients qualify for treatment, however, and a high recurrence rate follows surgery.[3,4] Therefore, the development of new treatment strategies is a high clinical priority.

Aspartate-β-hydroxylase (ASPH), also known as aspartyl-asparaginyl-β-hydroxylase, is a type 2 transmembrane protein that belongs to the a-ketoglutarate-dependent dioxygenase family.[5] It is a highly conserved enzyme, which catalyzes the hydroxylation of aspartyl and asparaginyl residues in epidermal growth factor-like domains of proteins including Notch and Notch homologs.[6-8] ASPH is over expressed in HCC compared to normal liver tissue; over expression produces a malignant phenotype characterized by increased cell motility and invasion.[6,9] Reportedly, the level of ASPH expression in HCC correlates significantly with postoperative prognosis.[10]

SUMMARY OF THE INVENTION

The invention provides a solution to the longstanding problem of an alternative to chemotherapy for treatment of patients diagnosed with cancer.

For example, hepatocellular carcinoma (HCC) has a poor prognosis due to high recurrence rate and lack of effective systemic therapy. Aspartate-β-hydroxylase (ASPH) is a highly conserved transmembrane protein, which is over expressed in HCC and promotes malignant phenotypes. The methods for cancer immunotherapy described herein induce an effective immune response that specifically targets tumor cells. While T cell responses specific for a tumor-associated antigen (TAA) are often observed, the TAA has not been sufficiently robust to affect clinical outcomes. The invention provides an improved ASPH-based immunotherapy. In particular, both HLA class I- and class II-restricted peptides, derived from ASPH, induced T cell activation in HCC. ASPH peptides elicited antigen-specific activation of CD4+ and CD8+ T cells among human PBMCs indicating that ASPH contains both HLA class I- and class II-restricted epitopes which are suitable for HCC immunotherapy.

Accordingly, the present invention includes a composition comprising a therapeutically effective amount of a purified ASPH peptide. For example, the peptide comprises at least 7 amino acids in length (e.g., at least 8 amino acids or at least 9 amino acids) and fewer amino acids than the full length ASPH protein and wherein the peptide comprises an HLA class I or class II-restricted epitope sequence. The sequences are preferably contiguous amino acids of the full-length ASPH protein. For example, the peptide comprises the HLA class II restricted sequence of TGYTELVKSLERNWKLI (SEQ ID NO:11). In another example, the peptide comprises the HLA class I restricted sequence of YPQSPRARY (SEQ ID NO:26). A purified or isolated vaccine peptide does not contain amino acids that flank the reference sequence in the naturally-occurring full-length ASPH protein. The reference sequence is identified by a SEQ ID number.

In preferred embodiments, the vaccine contains at least 2 peptides, e.g., the vaccine composition contains 5, 10, 15, 20 or more different ASPH peptides. An exemplary vaccine contains 10-15 different peptides selected from those listed and described herein. For example, an ASPH peptide (or combination/mixture of peptides) is selected from a group consisting of SEQ ID NOs: 1-45. A "therapeutically effective amount" of an ASPH peptide is an amount effective to induce an immunogenic response in the recipient. In some examples, the immunogenic response is adequate to inhibit (including prevent) or ameliorate signs or symptoms of disease or condition (such as an ASPH-expressing tumor), including adverse health effects or complications thereof. Either humoral immunity or cell-mediated immunity or both can be induced by the ASPH peptide (for example in an immunogenic composition) disclosed herein. In some examples, the vaccine composition does not include peptides characterized by an amino acid sequence that stimulate(s) Treg cells.

ASPH-expressing tumors include most tumor types such as tumors of gastrointestinal tissues (e.g., esophagus, stomach, colon), pancreas, liver (e.g., cholangiocellular carcinoma, hepatocellular carcinoma), breast, prostate, cervix, ovary, fallopian tube, larynx, lung, thyroid, gall bladder, kidney, bladder, and brain (e.g., glioblastoma) as well as numerous others described below. ASPH-expressing tumors include primary tumors that express an increased level of ASPH compared to normal tissue as well as tumors that arise by metastasis from such ASPH-overexpressing primary tumors.

Also within the invention is a vaccine that includes a composition described herein. Selected peptides, polypeptides, nucleic acid sequences or combination of thereof peptides are then combined in a vaccine composition. A suitable vaccine preferably contains between 1 and 20 peptides, more preferably 1, 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 12, 13 or 14 different peptides. Alternatively, a suitable vaccine will preferably contain between 1 and 20 nucleic acid sequences, more preferably 1, 2, 3, 4, 5, 6, 7, 8, 9, 10, 11, 12, 13, 14, 15, 16, 17, 18, 19, or 20 different nucleic acid sequences, further preferred 6, 7, 8, 9, 10 11, 12, 13, or 14 different nucleic acid sequences, and most preferably 12, 13 or 14 different nucleic acid sequences.

No particular length is implied by the term "peptide". For example, the ASPH peptide is less than 25 amino acids in length, e.g., less than or equal to 25, 24, 23, 22, 21, 20, 19, 18, 17, 16, 15, 14, 13, 12, 11, 10, 9, 8, 7, 6 or 5 amino acids in length. For example, the peptides are in the range of 7-10 amino acids in length, e.g., at least 8 amino acids in length or at least 9 amino acids in length. The ASPH peptides can be polymers of L-amino acids, D-amino acids, or a combination of both.

The vaccine is useful as a prophylactic vaccine or a therapeutic vaccine.

Any vaccine composition of the present invention may further comprise a pharmaceutical carrier, adjuvant or other co-ingredient. An adjuvant is a compound, composition, or substance that when used in combination with an immunogenic agent (such as an ASPH peptide disclosed herein) augments or otherwise alters or modifies a resultant immune response. In some examples, an adjuvant increases the titer of antibodies or the level of T cell activation induced in a subject by the immunogenic agent. In another example, if the antigenic agent is a multivalent antigenic agent, an adjuvant alters the particular epitopic sequences that are specifically bound by antibodies induced in a subject.

Exemplary adjuvants include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole lympet protein, hemocyanin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), E. coli heat-labile toxin (LT), Cholera toxin (CT), ceramides, and combinations thereof. Representative adjuvants that are well known and suitable for human use include aluminum salts (aluminum hydroxide, aluminum phosphate and aluminum potassium sulfate) as well as Monophosphoryl lipid A.

The pharmaceutically acceptable vehicle or carrier includes, but is not limited to, solvent, emulsifier, suspending agent, decomposer, binding agent, excipient, stabilizing agent, chelating agent, diluent, gelling agent, preservative, lubricant, surfactant, adjuvant or other suitable vehicle. Vaccine compositions are administered using methods known in the art, e.g., by injection, infusion, or by ingestion. For example, the vaccine is administered intra-muscularly, subcutaneously, intradermally, and/or orally.

Also within the invention is a cell line that expresses one or more ASPH peptides described herein.

A method for reducing growth of an ASPH-expressing tumor in a subject involves administering to the subject a composition of the invention (or a vaccine of the invention). Growth of an ASPH-expressing tumor is reduced after administration of such a composition or vaccine. For example, tumor growth and/or tumor mass or burden is reduced by 10%, 20%, 50%, 75%, 2-fold, 5-fold, 10-fold, or more than those without any treatment. The methods are used to reduce and eliminate ASPH-expressing tumors from mammalian subjects, such as human patients. The compositions and methods are also suitable for use in companion animals and livestock, e.g., canine, feline, equine, bovine, or porcine subjects.

A method of inhibiting tumor growth in a mammal is carried out by identifying a subject suffering from an ASPH-expressing tumor, and administering to the subject a composition or a vaccine of the invention. A method of preventing development of a tumor in a mammal, comprises the step of identifying a subject at risk of developing an ASPH-expressing tumor (such as one with a family history of cancer), and administering to the subject a composition or a vaccine of the invention. A method of preventing metastasis of an ASPH-expressing tumor is carried out by identifying a subject suffering from an ASPH-expressing tumor, and administering to the subject a composition or a vaccine of the invention, as described above.

Individual patients or subjects to be treated may be characterized by determining their pattern of expression of different class II or class I HLA molecules. Thus, the individual to be treated is optionally screened to evaluate their HLA make-up, e.g., to determine which HLA molecules they express and/or to determine which of the peptides, e.g., SEQ ID NOs. 1-45, are most suitable to include in a vaccine composition by virtue of HLA molecule/candidate vaccine peptide binding or immune cell activation. Thus, the method may further comprise a step of selecting one or more peptides from the group consisting of SEQ ID NOs: 1-45. A patient-derived immune cell or population of immune cells, e.g., PBMC or a population of purified T cells, is contacted with a purified peptide and immune activation of the cells is determined. Alternatively, binding of the peptide to patient cells (or the HLA molecule expressed by the patient) is measured. A peptide selected for inclusion into a vaccine preparation is characterized as one that elicits an HLA class I or class II-restricted T cell response. For example, the selected peptide elicits a HLA-DRB1-restricted ASPH T cell response, e.g., the T cell response is restricted to one or more of HLA-DRB1 alleles selected from the group consisting of DRB1*0101, DRB1*0301, DRB1*0401, DRB1*0701, DRB1*0801, DRB1*1101, DRB1*1301, and DRB1*1501. Alternatively or in addition, the selected peptide elicits an HLA-A or HLA-B restricted ASPH T cell response. For example, the T cell response is restricted to one or more HLA-A alleles selected from the group consisting of A*0101, A*0201, A*0301, A*2402, B*0702, and B*4403 and/or the T cell response is restricted to one or more HLA-B alleles selected from the group consisting of B*0702, and B*4403. In some preferred embodiments, the vaccine composition contains peptide(s) that are HLA class II restricted (to elicit a helper T cell response) as well as peptide(s) that are HLA class I restricted (to elicit a cytotoxic T cell response).

Any method described herein may also include a combination therapy prior to, concurrently or subsequent to the administration step. "Combination therapy" also embraces the administration of the therapeutic agents as described above (a composition or a vaccine that includes at least one ASPH peptide) in further combination with other biologically active ingredients and additional therapies (e.g., surgery or radiation treatment). Where the combination therapy further comprises an additional treatment, the additional treatment may be conducted at any suitable time so long as a beneficial effect from the co-action of the combination of the therapeutic agents and additional treatment is achieved. For example, in appropriate cases, the beneficial effect is still achieved when the additional treatment is temporally removed from the administration of the therapeutic agents, perhaps by days or even weeks. For example, the additional therapies include trans-arterial embolization (TAE), trans-arterial chemoembolization (TACE), radioembolization (RE) and/or local ablation.

The polypeptides and other compositions of the invention are purified. For example, a substantially pure ASPH polypeptide or variant thereof is preferably obtained by expression of a recombinant nucleic acid encoding the polypeptide or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, ASPH. Purity is measured by any appropriate method, e.g., column chromatography, polyacrylamide gel electrophoresis, or HPLC analysis. Accordingly, substantially pure polypeptides include recombinant polypeptides derived from a eucaryote but produced in *E. coli* or another procaryote, or in a eucaryote other than that from which the polypeptide was originally derived.

In some preferred embodiments, the vaccine peptide is characterized by a sequence of contiguous amino acids located in the carboxy-terminal portion of full-length ASPH, e.g., the peptide contains at least 7, 8, or 9 contiguous amino acids of the ASPH catalytic domain, e.g., in the region of containing a catalytic domain of HAAH (e.g., amino acids 650-700 of SEQ ID NO:46). In another example, the vaccine peptide is characterized by a sequence of contiguous amino acids located in the amino-terminal portion of the full-length ASPH protein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A: representative flow cytometric analyses.

DETAILED DESCRIPTION OF THE INVENTION

Figure 1A:
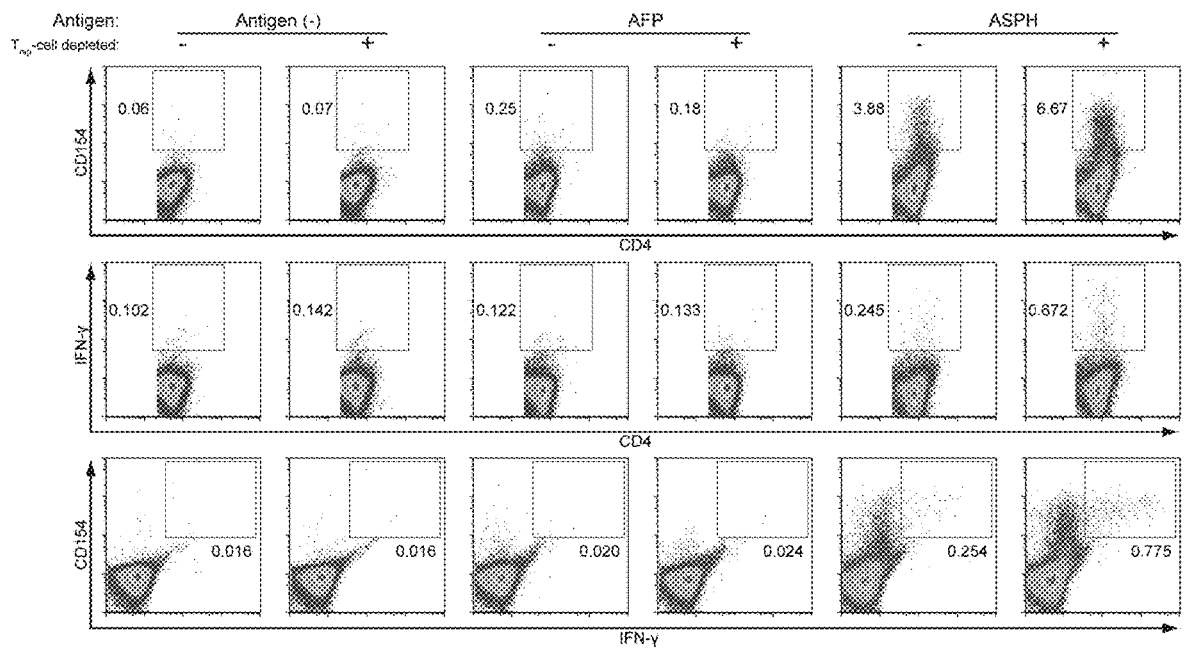
FIGS. 1A and C are histograms, and Figures B and D are dot plots. ASPH-specific T cell responses in HCC patients. CD25-depleted or non-depleted, pan T cells purified from the PBMCs of HCC patients (HCC #1-5) were co-cultured with monocyte-derived DCs loaded with recombinant ASPH, AFP or no antigen (control). After 8 days incubation, the T cells were collected and re-stimulated by co-culture with DCs loaded with the same antigen. The response of $CD4^+$ T cells was evaluated by quantifying the percentage of $CD154^+$, IFN-$\gamma^+$, and IFN-$\gamma^+CD154^+$ cells.
Figure 1B:
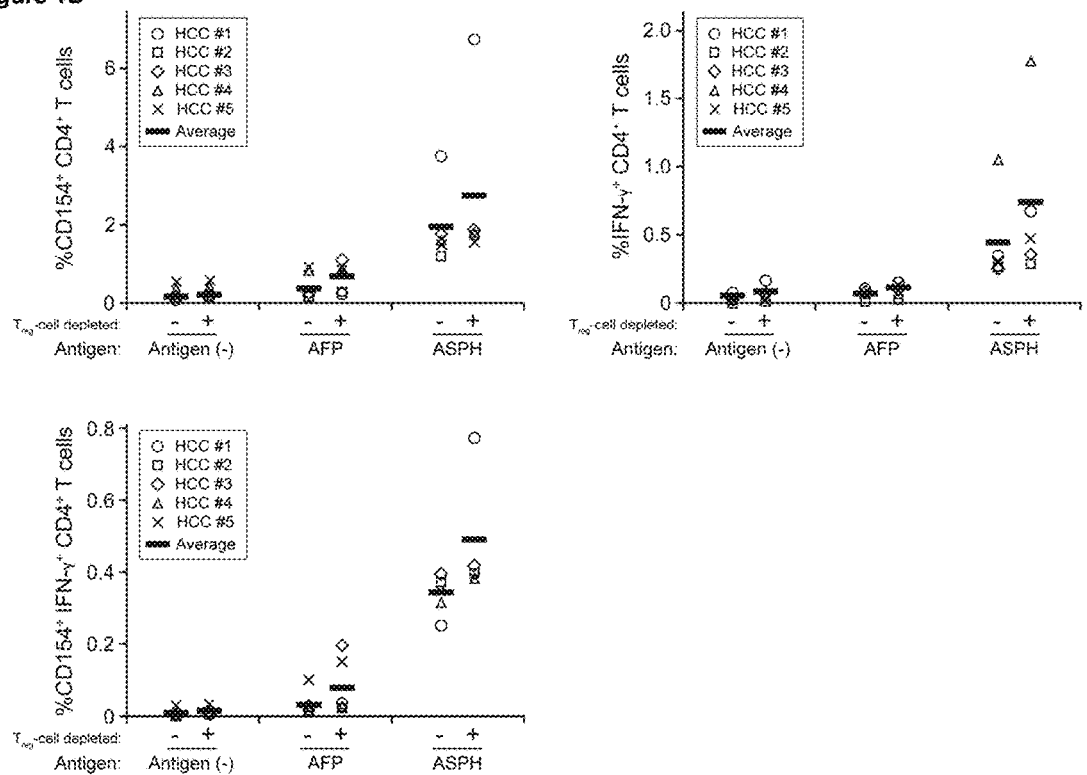
FIG. 1B: summary of the analyses of 5 HCC patients). The response of $CD8^+$ CTL was evaluated by quantifying the percentage of $CD137^+$ and IFN-$\gamma^+$ cells.

Individual purified HLA class I and II peptides of ASPH induced human peptide specific CD4+ helper and CD8+ cytotoxic T cell responses. Since ASPH is highly expressed on many solid tumors, such as hepatocellular carcinoma, cholangiocarcinoma, pancreatic tumors, breast, prostate, colon, lung and gastric cancers, these peptides are useful for vaccine to induce the host immune response against ASPH expressing cancers. This invention involves an ASPH peptide based prophylactic and therapeutic vaccine to inhibit or reduce ASPH-expressing tumors.

Prior to the invention, the response of human cytotoxic CD8+ T lymphocytes (CTL) to ASPH was unknown. The data described herein first demonstrated that full-length ASPH induced significant activation of CTLs, as well as CD4+ helper T cells, obtained from HCC patients. Next, immunoinformatics tools were used to determine 15 HLA-DRB1-restricted immunogenic consensus sequences (ICS, each composed of multiple epitopes) contained in ASPH. These ICS were synthesized as peptides and their capacities to bind multiple HLA-DRB1 alleles were determined. Thirty HLA class I-restricted ASPH epitopes were also determined and synthesized. Subsequently, each HLA class I- and class II-restricted peptide was evaluated and demonstrated to be immunogenic for HCC patients. The results of these analyses led to the development of an ASPH epitope-based vaccine for HCC immunotherapy.

HCC has a poor prognosis due to high recurrence rate and lack of effective systemic therapy. ASPH is a highly conserved transmembrane protein, which is over expressed in HCC and promotes malignant phenotypes. Immunization with ASPH-loaded dendritic cells (DCs) has anti-tumor effects in a murine HCC model. Moreover, ASPH induces a significant increase in antigen-specific CD4+ T cells in cultures of human peripheral blood mononuclear cells (PBMCs) indicating a utility of ASPH-based immunotherapy against HCC.

Monocyte-derived DCs generated from the PBMCs of HCC patients were loaded with ASPH. Helper CD4+ T cells and CD8+ cytotoxic T lymphocytes (CTLs) were co-incubated with the DCs. Subsequently T cell activation was evaluated by flow cytometric analysis. Immunoinformatics tools were used to determine HLA class I- and class II-restricted ASPH sequences, and the corresponding peptides were synthesized. The immunogenicity of each peptide in cultures of human PBMCs was determined by IFN-γ enzyme-linked immunospot assay.

ASPH-loaded DCs activated both CD4+ and CD8+ T cells contained within the PBMC population derived from HCC patients. Furthermore, the HLA class I- and class II-restricted ASPH peptides were significantly immunogenic in PBMC cultures. Both HLA class I- and class II-restricted peptides derived from ASPH induced T cell activation in HCC. These results indicate the efficacy of an ASPH peptide-based therapeutic vaccine for HCC and other ASPH over-expressing tumors.

ASPH Peptides

The ASPH vaccine peptides bind to human HLA molecules and stimulate an ASPH-specific anti-tumor immune response, thereby reducing tumor burden/tumor mass, reducing metastases, and conferring a clinical benefit to the patient suffering from an ASPH-expressing tumor. Methods for measuring binding of peptides to HLA molecules are well known in the art, e.g., Parker et al., 1994, Journal of Immunology 152:163. Methods for measuring T-cell mediated immune responses, e.g., activation of CD8+ cytotoxic T cells and/or helper CD4+ T cells are also well known in the art, e.g., detection of secreted immune activation markers and/or cell surface activation markers in response to immunostimulatory ASPH peptide antigens. Exemplary protocols are described herein.

Peptide variants that preserve antigenic function are also within the invention. For example, a variant may contain an amino acid residue at a particular position in the sequence which has been substituted by other amino acids or may include an additional residue or residues between two residues of the reference peptide as well as a deletion one or more residues from the reference sequence provided that the peptide retain the function of stimulating an ASPH-specific anti-tumor immune response (e.g., activation of ASPH-specific T cells). Such a peptide variant will have at least about 71%-75% amino acid sequence identity; at least about 76%-79% amino acid sequence identity; at least about 80% amino acid sequence identity, at least about 81% amino acid sequence identity, at least about 82%, 83%, 84%, 85%, 86%, 87%, 88%, 89%, 90%, 91%, 92%, 93%, 94%, 95%, 96%, 97%, 98% amino acid sequence identity and at least about 99% amino acid sequence identity with a full-length sequence.

In some examples, the variants contain conservative substitutions. Conservative substitutions are shown in the table below. Conservative substitutions whereby an amino acid of one class is replaced with another amino acid of the same type fall within the scope of the subject invention so long as the substitution does not materially alter the biological activity of the compound.

| Exemplary substitutions | | |
|---|---|---|
| Original residue | Exemplary substitutions | Preferred substitutions |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |

-continued

Exemplary substitutions

| Original residue | Exemplary substitutions | Preferred substitutions |
|---|---|---|
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

The polypeptides of the invention can be either synthesized in vitro or expressed recombinantly from polynucleotide sequences. The polypeptides of the invention can be readily synthesized in vitro using polypeptide chemistry. For example, polypeptide synthesis can be carried out in a stepwise manner on a solid phase support using an automated polypeptide synthesizer, such as a Rainin Symphony Peptide Synthesizer, Advanced Chemtech Peptide Synthesizer, Argonaut Parallel Synthesis System, or an Applied Biosystems Peptide Synthesizer. The peptide synthesizer instrument combines the Fmoc chemistry with HOBt/HBTU/DIEA activation to perform solid-phase peptide synthesis.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The following materials and methods were used to generate the date described herein.

Recombinant ASPH and ASPH Peptides

Full-length human ASPH (GenBank Accession No. S83325; Version: S83325.1 hereby incorporated by reference) was cloned into the EcoRI site of the pcDNA vector (Invitrogen, Carlsbad, Calif.). Recombinant protein was produced in a Baculovirus system (Invitrogen) according to the manufacturer's instruction.[11,12]

SEQ ID NO 46 Human ASPH amino acid sequence

MAQRKNAKSSGNSSSSGSGSGSTSAGSSSPGARRETKHGGHKNG

RKGGLSGTSFFTWFMVIALLGVWTSVAVVWFDLVDYEEVLGKLG

IYDADGDGDFDVDDAKVLLGLKERSTSEPAVPPEEAEPHTEPEE

QVPVEAEPQNIEDEAKEQIQSLLHEMVHAEHVEGEDLQQEDGPT

GEPQQEDDEFLMATDVDDRFETLEPEVSHEETEHSYHVEETVSQ

DCNQDMEEMMSEQENPDSSEPVVEDERLHHDTDDVTYQVYEEQA

VYEPLENEGIEITEVTAPPEDNPVEDSQVIVEEVSIFPVEEQQE

VPPETNRKTDDPEQKAKVKKKKPKLLNKFDKTIKAELDAAEKLR

KRGKIEEAVNAFKELVRKYPQSPRARYGKAQCEDDLAEKRRSNE

VLRGAIETYQEVASLPDVPADLLKLSLKRRSDRQQFLGHMRGSL

LTLQRLVQLFPNDTSLKNDLGVGYLLIGDNDNAKKVYEEVLSVT

PNDGFAKVHYGFILKAQNKIAESIPYLKEGIESGDPGTDDGRFY

FHLGDAMQRVGNKEAYKWYELGHKRGHFASVWQRSLYNVNGLKA

QPWWTPKETGYTELVKSLERNWKLIRDEGLAVMDKAKGLFLPED

ENLREKGDWSQFTLWQQGRRNENACKGAPKTCTLLEKFPETTGC

RRGQIKYSIMHPGTHVWP<u>HTGPTNCRLRMHLGLVIPK</u>EGCKIRC

ANETRTWEEGKVLIFDDSFEHEVWQDASSFRLIFIVDVWHPELT

PQQRRSLPAI

His motif is underlined; conserved sequences within the catalytic domain are designated by bold type. Additional information regarding ASPH is found in U.S. Pat. No. 6,783,758, hereby incorporated by reference.

SEQ ID NO: 47 Human ASPH cDNA sequence (GENBANK Accession No. S83325; codon encoding initiating methionine is underlined).

```
  1  cggaccgtgc a<u>atg</u>gcccag cgtaagaatg ccaagagcag cggcaacagc agcagcagcg
 61  gctccggcag cggtagcacg agtgcgggca gcagcagccc cggggcccgg agagagacaa
121  agcatgagg acacaagaat gggaggaaag gcggactctc gggaacttca ttcttcacgt
181  ggtttatggt gattgcattg ctgggcgtct ggacatctgt agctgtcgtt tggtttgatc
241  ttgttgacta tgaggaagtt ctaggaaaac taggaatcta tgatgctgat ggtgatggag
301  attttgatgt ggatgatgcc aaagttttat taggacttaa agagagatct acttcagagc
361  cagcagtccc gccagaagag gctgagccac acactgagcc cgaggagcag gttcctgtgg
421  aggcagaacc ccagaatatc gaagatgaag caaagaaca aattcagtcc cttctccatg
481  aaatggtaca cgcagaacat gttgagggag aagacttgca acaagaagat ggacccacag
541  gagaaccaca acaagaggat gatgagtttc ttatggcgac tgatgtagat gatagatttg
601  agacctggaa acctgaagta tctcatgaag aaaccgagca tagttaccac gtggaagaga
661  cagtttcaca agactgtaat caggatatgg aagagatgat gtctgagcag gaaaatccag
```

```
-continued
 721  attccagtga accagtagta gaagatgaaa gattgcacca tgatacagat gatgtaacat 781  accaagtcta tgaggaacaa gcagtatatg aacctctaga aaatgaaggg atagaaatca 841  cagaagtaac tgctccccct gaggataatc ctgtagaaga ttcacaggta attgtagaag 901  aagtaagcat ttttcctgtg gaagaacagc aggaagtacc accagaaaca aatagaaaaa 961  cagatgatcc agaacaaaaa gcaaaagtta agaaaaagaa gcctaaactt ttaaataaat 1021  ttgataagac tattaaagct gaacttgatg ctgcagaaaa actccgtaaa aggggaaaaa 1081  ttgaggaagc agtgaatgca tttaaagaac tagtacgcaa ataccctcag agtccacgag 1141  caagatatgg gaaggcgcag tgtgaggatg atttggctga gaagaggaga agtaatgagg 1201  tgctacgtgg agccatcgag acctaccaag aggtggccag cctacctgat gtccctgcag 1261  acctgctgaa gctgagtttg aagcgtcgct cagacaggca acaatttcta ggtcatatga 1321  gaggttccct gcttaccctg cagagattag ttcaactatt tcccaatgat acttccttaa 1381  aaaatgacct tggcgtggga tacctcttga taggagataa tgacaatgca aagaaagttt 1441  atgaagaggt gctgagtgtg acacctaatg atggctttgc taaagtccat tatggcttca 1501  tcctgaaggc acagaacaaa attgctgaga gcatcccata tttaaaggaa ggaatagaat 1561  ccggagatcc tggcactgat gatgggagat tttatttcca cctgggggat gccatgcaga 1621  gggttgggaa caaagaggca tataagtggt atgagcttgg gcacaagaga ggacactttg 1681  catctgtctg gcaacgctca ctctacaatg tgaatggact gaaagcacag ccttggtgga 1741  ccccaaaaga aacgggctac acagagttag taaagtcttt agaaagaaac tggaagttaa 1801  tccgagatga aggccttgca gtgatggata aagccaaagg tctcttcctg cctgaggatg 1861  aaaacctgag ggaaaaaggg gactggagcc agttcacgct gtggcagcaa ggaagaagaa 1921  atgaaaatgc ctgcaaagga gctcctaaaa cctgtacctt actagaaaag ttccccgaga 1981  caacaggatg cagaagagga cagatcaaat attccatcat gcaccccggg actcacgtgt 2041  ggccgcacac agggcccaca aactgcaggc tccgaatgca cctgggcttg gtgattccca 2101  aggaaggctg caagattcga tgtgccaacg agaccaggac ctgggaggaa ggcaaggtgc 2161  tcatctttga tgactccttt gagcacgagg tatggcagga tgcctcatct ttccggctga 2221  tattcatcgt ggatgtgtgg catccggaac tgacaccaca gcagagacgc agccttccag 2281  caatttagca tgaattcatg caagcttggg aaactctgga gaga
```

ASPH ICS were determined.[13,14] The entire protein was parsed into overlapping 9-mer frames and each frame was evaluated using EpiMatrix for its potential to bind a panel of eight common HLA-DRB1 alleles (DRB1*0101, DRB1*0301, DRB1*0401, DRB1*0701, DRB1*0801, DRB1*1101, DRB1*1301, and DRB1*1501), which represent >95% of the MHC diversity in the human population.[15] HLA-DRB1-restricted ICS were constructed using EpiAssembler, an algorithm that maximizes epitope density by assembling potentially immunogenic 9-mers into 18-25 amino acid stretches.[16] Additionally, all parsed 9-mers were scored for their potential to bind a panel of six common class I "supertype" alleles; A*0101, A*0201, A*0301, A*2402, B*0702, and B*4403, which cover over 95% of the human population.[17] Based upon these predictions, the peptide sequences were synthesized using FMOC chemistry and purified >85% by HPLC (21$^{st}$ Century Biochemicals, Marlboro, Mass.); each was dissolved in 100% DMSO (100 µg/µl) and stored at −80° C. The amino acid sequences of the HLA-DRB1-restricted peptides and HLA class I-restricted peptides are shown in Table I and Table II, respectively.

Healthy Blood Donors and HCC Patients

Blood samples were obtained from 12 HCC patients (HCC #1-12) and 5 healthy blood donors (HD #1-5). The peripheral blood mononuclear cells (PBMCs) were purified from whole blood of the HCC patients using known methods.[11] HLA typing on DNA extracted from each sample was performed using known methods.

Used, de-identified whole-blood leukocyte reduction filters (blood filters; Sepacell RZ-2000, Baxter Healthcare Corporation, Irvine Calif.), served as the source of PBMCs derived from blood donated with informed consent by healthy volunteers. The PBMCs were recovered by back-flushing the filters according to the methods of Meyer et al. and purified by centrifugation on Ficoll-Paque Plus (1.077; Pharmacia, Uppsala, Sweden) gradient using known methods.[18,19]

Generation of DCs

DCs were generated using known methods.[11,20] Monocytes were isolated from PBMCs using anti-CD14 microbeads (Miltenyi Biotec, Auburn, Calif.) and cultured for 5 days in X-VIVO 15 medium (Lonza, Walkerville, Md.) supplemented with human GM-CSF (R&D Systems, Minneapolis, Minn.) and IL-4 (R&D Systems). ASPH (1 µg/ml)

was added on day 5. On the next day, TNF-α (R&D Systems) was added to stimulate DC maturation and the cells were incubated for another 48 hours. DCs incubated with α-fetoprotein (AFP; Zynaxis Cell Science, Malvern, Pa.) or alone served as the control. Mature, epitope-expressing DCs were collected at the end of the incubation period and used in the experiments described.

Induction of Epitope-Specific T Cells

Epitope-specific T cells were induced according to known methods.[21] Briefly, $2.5 \times 10^5$ PBMCs/200 μl X-VIVO 15 medium supplemented with 1 mM L-glutamine, 100 U/ml penicillin, 100 μg/ml streptomycin, and 50 U/ml recombinant human IL-2 (R&D Systems) in round-bottom 96-well plates were cultured for 2 weeks with 10 μg/ml individual peptide. When mature DCs were used as antigen-presenting cells, the T cells were isolated from PBMCs by negative selection using the Pan T Cell Isolation Kit II (Miltenyi Biotec). Regulatory $T_{(reg)}$ cells were removed by the addition of anti-CD25 microbeads (Miltenyi Biotec) where indicated. $T_{reg}$ cell-depleted or non-depleted T lymphocytes $(2.4 \times 10^6)$ were co-cultured for 8 days with $4 \times 10^4$ mature DCs loaded with relevant antigen in 24-well plates.[11]

Blocking of T Cell Response

To demonstrate the contribution of HLA molecules to ASPH peptide-dependent T cell activation, the cells were incubated with antibodies specific for HLA class I (clone W6/32; BioLegend, San Diego, Calif.) or HLA-DR (clone L432; BioLegend) (15 μg/ml) for 1 hour at 37° C. prior to analyses.

Flow Cytometric Analysis

Flow cytometric analysis was conducted.[11] Intracellular cytokine staining was performed to evaluate T cell activation. Conjugated mouse monoclonal antibodies specific for the following determinants were used: CD4 (clone OKT4; BioLegend, San Diego, Calif.), CD8a (clone RPA-T8; BioLegend), CD137 (clone 4B4-1; BD Biosciences, San Diego, Calif.), CD154 (clone TRAP1; BD Biosciences), and IFN-γ (clone B27; BD Biosciences). Appropriate isotype controls were included in each analysis.

Enzyme-Linked Immunospot Assay

Human IFN-γ enzyme-linked immunospot (ELISpot) assays were performed as we described previously using a kit purchased from eBioscience (San Diego, Calif.) to determine T cell immune-reactivity.[21] Cells ($5 \times 10^4$/well) were added to ELISpot plates (Millipore, Bedford, Mass.) pre-coated with anti-IFN-γ capture antibody and incubated with peptides (10 μg/ml) for 20 hours. Subsequently, the plates were washed and incubated sequentially with biotinylated IFN-γ detection antibody then avidin-HRP. The plates were developed by adding substrate, 3-amino-9-ethyl carbazole, and the number of spots/well was quantified using a CTL-immunospot S5 UV Analyzer (Cellular Technology Limited, Shaker Heights, Ohio).

Enzyme-Linked Immunosorbent Assay

Enzyme-linked immunosorbent assays (ELISA) were performed to quantify IFN-γ in cell culture supernatants using a human IFN-γ ELISA kit (eBioscience).[11]

Statistical Analysis

Data are expressed as mean± SD. Differences between groups were assessed by the $\chi^2$-test, Fisher's exact test or the Mann-Whitney U test. A p value<0.05 was considered statistically significant. Data analyses were performed using StatView (version 5.0; SAS Institute Inc., Cary, N.C.).

Immunogenic Response of HCC Patients to ASPH

Figure 5A:
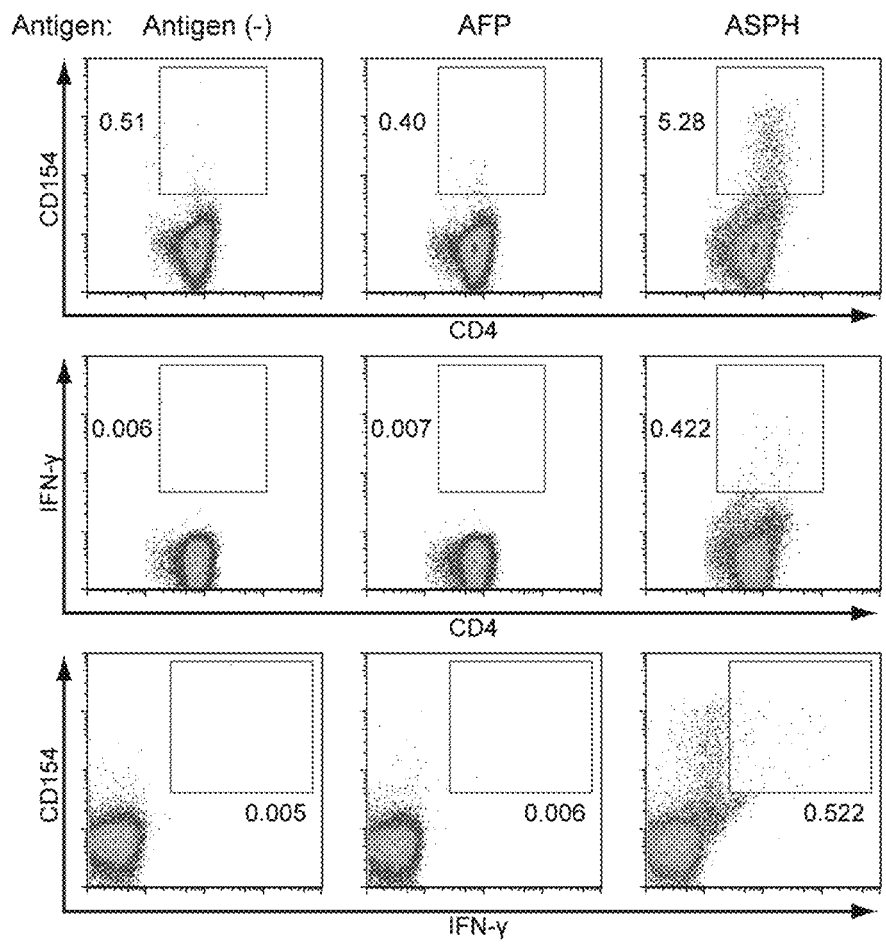
FIGS. 5A and B are histograms. ASPH protein-specific T cell response of a healthy blood donor. Pan T cells purified from the PBMCs of HD #1 were co-cultured with monocyte-derived DCs loaded or not loaded (control) with recombinant ASPH or AFP. After 8 days incubation, the T cells were collected and re-stimulated by culture with a fresh population of DCs loaded with the same antigen. The response of CD4+ T cells was evaluated by quantifying the percentage of CD154+, IFN-γ+, and IFN-γ+CD154+ cells within the total CD4+ T cell population (FIG. 5A). The response of CD8+ CTLs was evaluated by quantifying the percentage of CD137+ and IFN-γ+ cells within the total CD8+ T cell population (FIG. 5B). The percentage of cells in the gated area is shown.
Figure 5B:
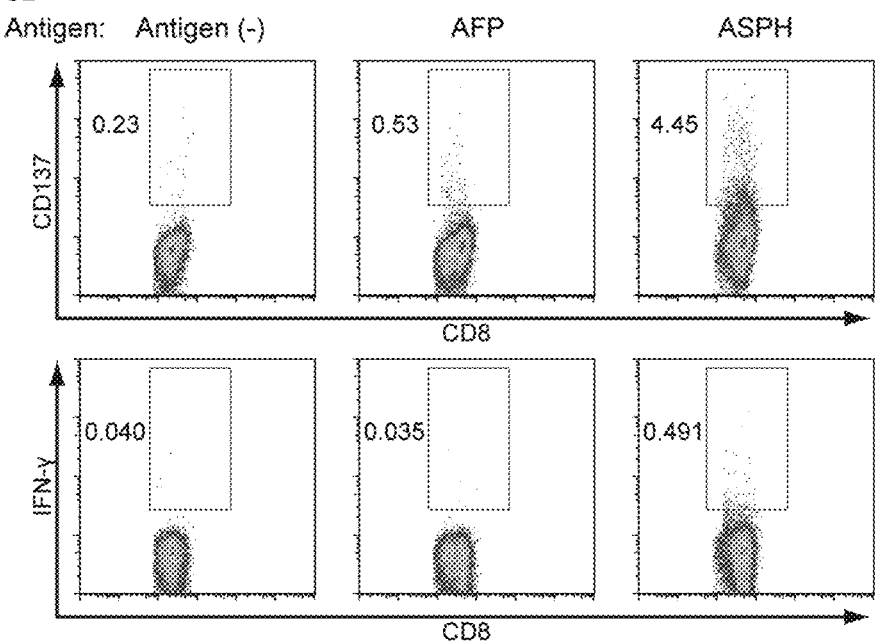

Experiments were undertaken to determine the capacity of ASPH to activate CD8+ CTLs, as well as helper CD4+ T cells, contained in the PBMC populations derived from HCC patients. The experimental procedure for evaluating ASPH-specific T cell activation was optimized using PBMCs derived from a healthy donor.[11] Pan T cells were co-cultured with autologous, ASPH-pulsed DCs; T cells co-incubated with AFP-pulsed or non-pulsed DCs served as controls. After 8 days culture, the T cells were collected and re-incubated with freshly prepared DCs pre-loaded with the same antigen; antigen-specific T cell activation was evaluated by flow cytometric analysis. In addition to IFN-γ, the expression of CD154 and CD137 was used as a surrogate marker for antigen-specific activation of CD4+ T cells and CD8+ CTLs, respectively.[22,23] These experiments revealed significant increases in the activation of both CD4+ T cells and CTLs in response to ASPH compared to AFP or no antigen (FIGS. 5A and B). Moreover, they support the premise that immunization with ASPH activates protein-specific CD4+ and CD8+ T cells in HCC patients.

Figure 1C:
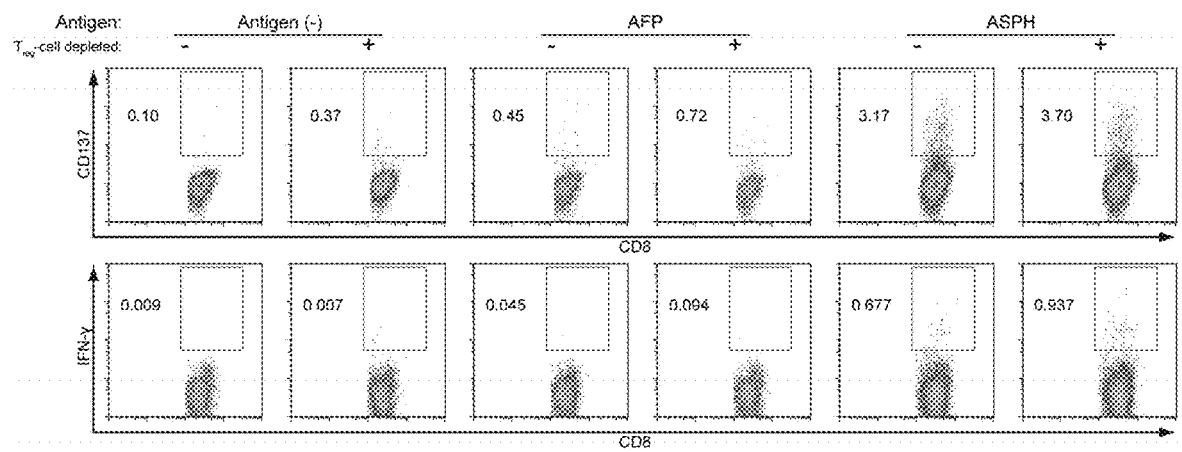
FIG. 1C: representative flow cytometric analyses.
Figure 1D:
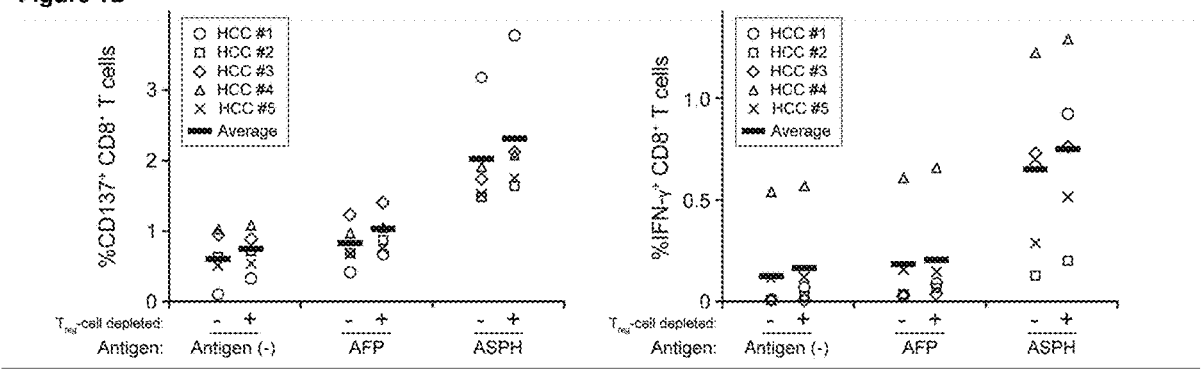
FIG. 1D: summary of the analyses in 5 HCC patients). The percentages of responsive cells in the ASPH sample are significantly greater than the percentages found in the AFP sample or antigen control, $p<0.05$ (FIGS. 1B and 1D); the $T_{reg}$ cell-depleted and non-depleted ASPH samples are significantly different from each other, $p<0.05$ (FIG. 1B).

Using the same experimental approach, ASPH-specific T cell activation was evaluated in PBMCs derived from five HCC patients (HCC #1-5) characterized in Table 3. As shown in FIGS. 1A and B, incubation with ASPH-pulsed DCs resulted in significant increases in CD4+CD154+ and CD4+IFN-γ+ T cells compared to incubation with AFP-pulsed or non-pulsed DCs. CD4+ T cells expressing both IFN-γ and CD154 were also expanded significantly. In addition, the percentage of CD8+ CTLs expressing CD137 and IFN-γ was significantly higher in co-cultures that contained ASPH-pulsed DCs compared to co-cultures that contained AFP-pulsed or non-pulsed DCs (FIGS. 1C and D). $T_{reg}$ cell depletion using anti-CD25 microbeads prior to co-culture enhanced ASPH-specific T cell activation.[20] These results, which demonstrate the ASPH-specific activation of CD4+ and CD8+ T cells among PBMCs derived from HCC patients, support the use of purified ASPH peptides in HCC immunotherapy for ASPH-overexpressing tumors.

Prediction and Validation of HLA-DRB1-Restricted ASPH Peptide Sequences

The demonstrated immunogenicity of purified ASPH peptides affords the development of an ASPH epitope-based anti-tumor vaccine. Both MHC class II-restricted (CD4+) and MHC class I-restricted (CD8+) T cells are preferably used for sustained anti-tumor immunity.[24,25] Initially, HLA-DRB1-restricted ICS composed of multiple epitopes and covering full-length human ASPH were determined and constructed using bioinformatics tools.[13,14] Fifteen promiscuous ISC, each capable of binding multiple HLA-DRB1 alleles representing >95% of the human population, were synthesized (Table I).[15]

Figure 2:
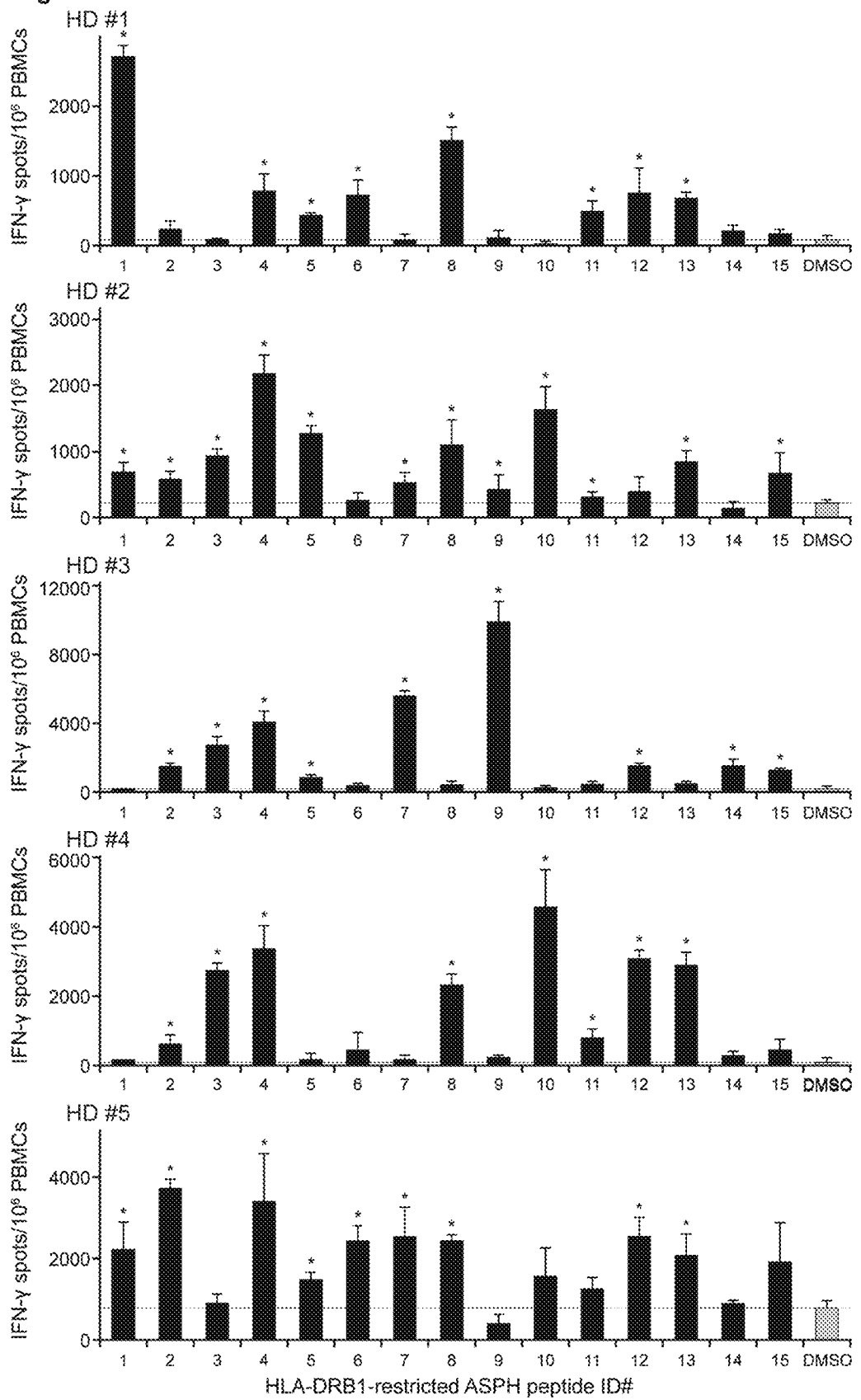
FIG. 2 is a bar graph. The response of healthy donors to predicted ASPH immunoconsensus sequences. PBMCs isolated from healthy donors (HD #1-5) were cultured with the single HLA-DRB1-restricted ASPH peptide (10 μg/ml) enumerated according to the list in Table I. The cells were collected after 2 weeks and the peptide-specific response was quantified by a standard IFN-$\gamma$ ELISpot assay. Values are expressed as the means±SD of triplicate determination. The dotted lines represent the level of control (0.1% DMSO). *Significantly greater than the control, $p<0.05$.

The validity of these predicted ASPH epitopes (ICS) was documented by demonstrating their ability to induce the response of naïve T cells contained within PBMC populations derived from 5 healthy blood donors (HD #1-5). The PBMCs obtained from each donor were transferred to multiple wells in a 96-well round bottom plate and cultured with a single, ASPH peptide sequence. After 2 weeks, the capacity of each sequence to induce a peptide-specific response was evaluated by IFN-γ ELISpot assay. As shown in FIG. 2, each peptide sequence induced a statistically significant increase in IFN-γ producing cells, albeit, the response to any single sequence varied among donors. While these ICS are promiscuous and bind multiple HLA-DRB1 alleles, it is likely that differences in the donors' MHC backgrounds contribute to this varied response. Notably, however, all the ASPH peptides exhibited immunogenicity in at least one healthy blood donor, and p322 (ID #4, Table I) was immunogenic for all 5 donors. p581 (ID #11, Table I) also emerged as a preferred peptide.

Figure 3A:
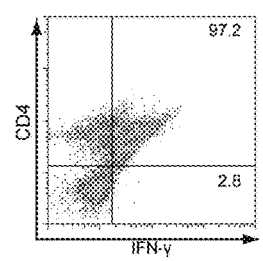
FIG. 3A is a histogram, FIGS. 3B and C are bar graphs.
Figure 3B:
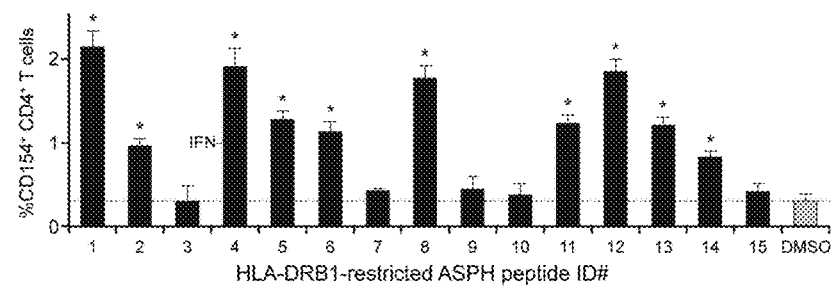
FIG. 3D is a line graph. Characterization of ASPH peptide-specific T cell responses. PBMCs obtained from patient HD #1 were cultured with the ASPH peptides indicated. After 2 weeks incubation, the cells were collected and re-cultured with the corresponding peptides for 20 hours, followed by analyses. p52-reactive PBMCs were stained and the percentage of IFN-$\gamma^+CD4^+$ T cells was determined by flow cytometric analysis (FIG. 3A). The percentage of CD154-expressing $CD4^+$ T cells assessed by flow cytometric analysis was determined as a measure of the response of cells to the ASPH peptide listed in accordance with Table I (FIG. 3B). The results are the means±SD of triplicate determinations; dotted lines represent the control (0.1% DMSO) values. *Significantly greater than control, $p<0.05$. PBMCs cultured 2 weeks with the peptides listed were not treated or pretreated with anti-HLA-A,B,C or anti-HLA-DR for 1 hour; the same corresponding peptide (10 μg/ml) was then added and IFN-$\gamma$ in the culture supernates collected after 5 days was quantified by ELISA (FIG. 3C). Results are the means±SD of triplicate determinations *Significantly less than non-antibody or anti-HLA-A,B,C-treated; $p<0.05$ Peptide titration assay for the immune response of ASPH peptides-specific cells (FIG. 3D). PBMCs, cultured 2 weeks with the ASPH peptides listed, were collected and reincubated with increasing concentrations of the same peptide. IFN-$\gamma$ in the culture supernates collected after 5 days was quantified by standard ELISA.
Figure 3C:
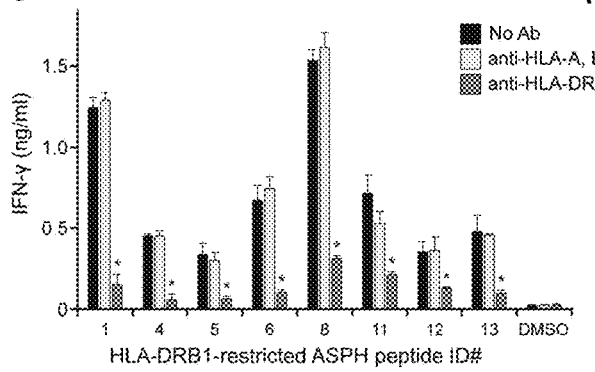
Figure 3D:
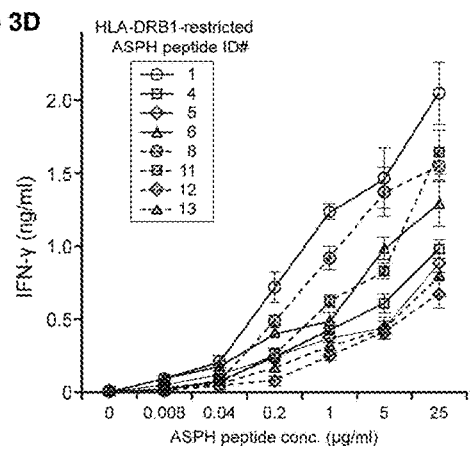

To quantify and characterize the IFN-γ-producing cells, the PBMCs derived from HD #1 following induction by p52 (ID #1, Table I) were stained and evaluated by flow cytometric analysis. As predicted, essentially all HLA-DRB1-restricted, p52-reactive, IFN-γ-producing cells expressed CD4 (FIG. 3A). In addition, CD154 expression was assessed as a measure of CD4+ T cells activation following incubation with each ASPH peptide (FIG. 3B). The pattern of CD154 expression was consistent with the IFN-γ ELISpot data presented above. HLA blocking experiments confirmed the dependence of ASPH peptide-induced IFN-γ production on HLA-DRB1 expression. IFN-γ production by the ASPH peptide-responsive cells was significantly abrogated by the presence of anti-HLA-DR, but not anti-HLA-class I, antibody (FIG. 3C). Titration experiments revealed dose-dependent increases in IFN-γ production following ASPH peptide stimulation (FIG. 3D). Together, these results substantiate the HLA-DR-restricted, dose-dependent CD4+ T cell responses induced by the ASPH peptides. IL-4 production was not observed following incubation with any of the ASPH peptide sequences indicating that these sequences induced Th1-like CD4+ T cell responses.

ASPH Peptide-Specific T Cell Activation in HCC Patients

Figure 4A:
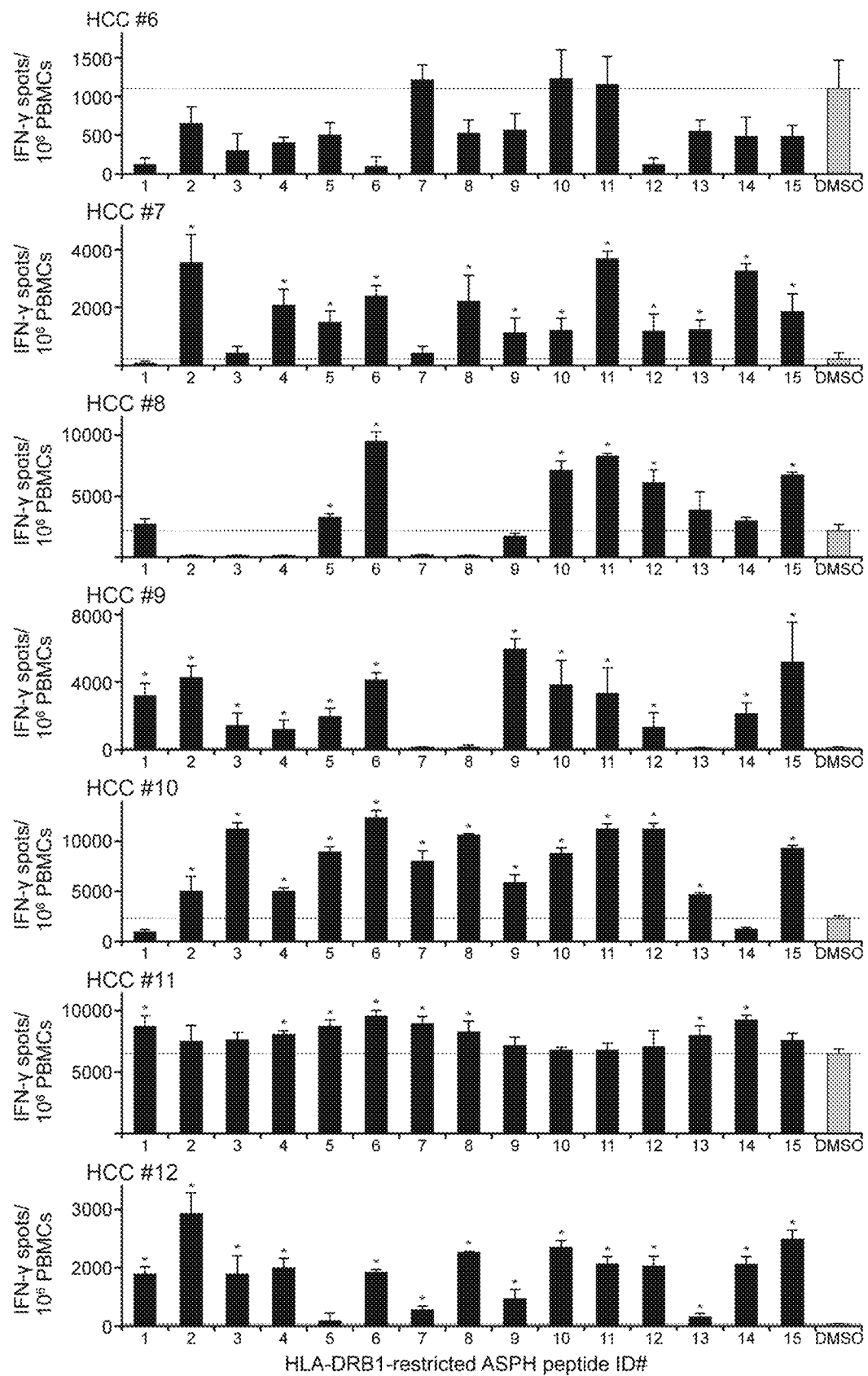
FIGS. 4A and B are bar graphs. HCC patient respond to ASPH peptides. PBMCs obtained from 7 HCC patients (HCC #6-12) were cultured for 2 weeks with HLA-DRB1-restricted (FIG. 4A) or HLA-class I-restricted (FIG. 4B) ASPH peptide compatible with the patients' HLA background (indicated in parentheses) and enumerated in accordance with Tables I and II. Peptide-specific T cell recognition was evaluated by IFN-$\gamma$ ELISpot assay. Values are the means±SD of triplicate determination. The dotted lines represent the level of control (0.1% DMSO). *Significantly greater than the control, $p<0.05$.

Based upon the results demonstrating the HLA-DRB1-restricted, ASPH ICS-specific T cell response of healthy blood donors, the response of CD4+ T cells derived from seven HCC patients (HCC #6-12) to the same peptides was evaluated. Each HLA class II-restricted peptide sequence induced a statistically significant increase in IFN-γ producing cells, though the response to individual peptides varied among patients (FIG. 4A). None of the peptides elicited a significant response in HCC patient #6. All the predicted ASPH peptides exhibited immunogenicity in at least one HCC patients, however, a pattern similar to that found in the healthy blood donors shown above.

Figure 4B:
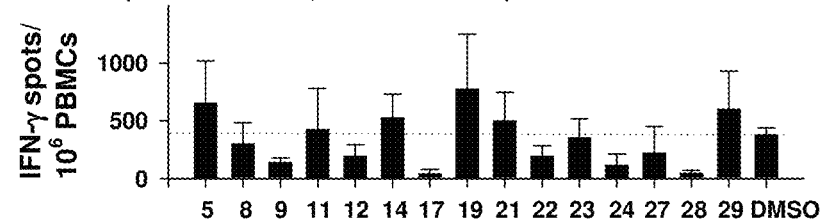
Figure 4B:
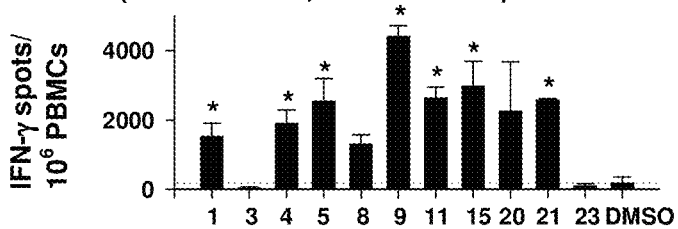
Figure 4B:
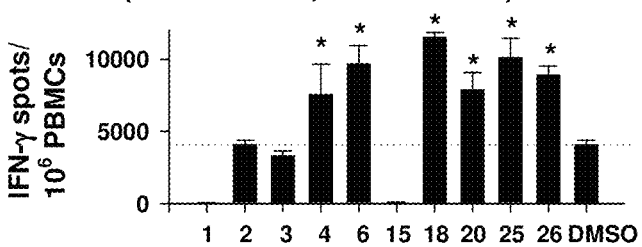
Figure 4B:
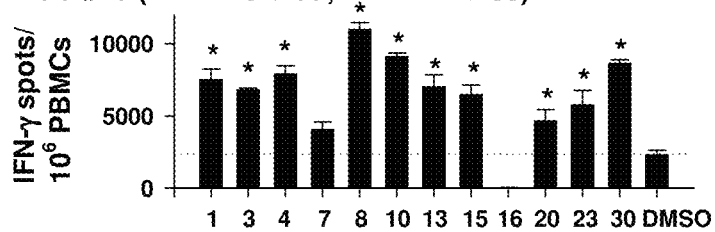
Figure 4B:
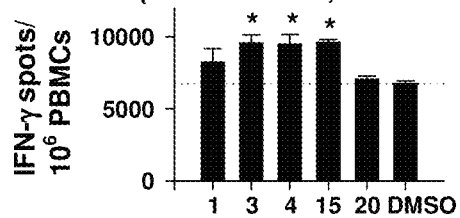
Figure 4B:
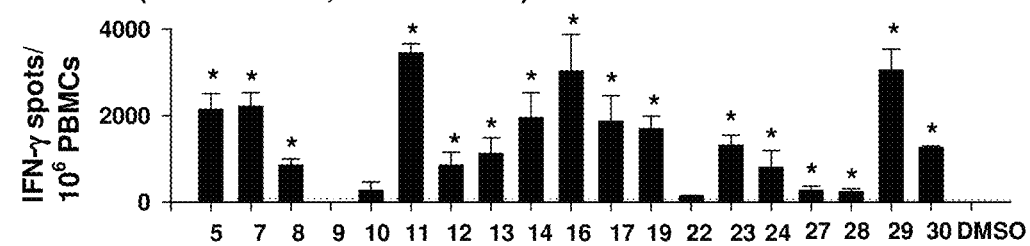

CD8+, as well as CD4+, T cells are required for anti-tumor immunity. As such, HLA class I-restricted ASPH-derived epitopes were also determined and 30 HLA-A- and HLA-B-restricted peptides were synthesized (Table II). The response of CD8+ CTLs derived from the HCC patients to the peptides compatible with their HLA class I alleles was subsequently evaluated. Histoincompatibility precluded including HCC patient #8 in this analysis. All the HLA class I-restricted peptides induced significant increases in IFN-γ producing cells albeit, as in the case of those restricted by HLA-DRB1, the response to individual peptides varied substantially among patients (FIG. 4B). HCC patient #6, for example, failed to exhibit a significant response to any peptide among a panel of 11 HLA-A*01/*03- and 5 HLA-B*07-restricted peptides. HCC patient #12, on the other hand, responded to 85% of the peptides compatible with his HLA background. ASPH 371 was determined to be a preferred class I restricted peptide.

Immunogenic ASPH Epitopes in HCC Patients

The aim of cancer immunotherapy is to induce an effective immune response that specifically targets tumor cells.[26] Success is predicated upon the existence of a tumor-associated antigen (TAA), which is uniquely over expressed in tumor tissue and elicits a specific immune response in the tumor-bearing host. To date, several HCC-related TAAs have been identified: AFP, glypican-3, and NY-ESO-1.[27-30] While T cell responses specific for these TAAs are often observed, however, they are not sufficiently robust to affect clinical outcomes. Although the factors that contribute to these unsatisfactory outcomes are complicated and require further explorations, one factor seems to be a diminished CD4+ helper T cell response. Both activated CD4+ T cells and CD8+ CTLs are required to maintain a sustained anti-tumor response.[24,25]

ASPH was found here to elicit the antigen-specific activation of CD4+ and CD8+ T cells among human PBMCs indicating that ASPH possesses both HLA class I- and class II-restricted epitopes making it useful for HCC immunotherapy. Such an approach utilizes an epitope-based vaccine for HCC, which consists of a combination of purified peptides (epitopes) capable of eliciting the robust responses of CD4+ and CD8+ T cells. Toward this end, immunoinformatics tools were used to identify 30 ASPH-derived HLA class I-restricted and 15 class II-restricted epitopes. These epitopes induced both CD8+ CTL and CD4+ T cell responses by six out of seven HCC patients indicating that these chosen ASPH peptides are useful for HCC immunotherapy. Notably, one patient (HCC #6) failed to respond to any of the epitopes compatible with her HLA background suggesting that she would not be a good candidate. Such a response profile of an individual patient provides basis for personalized treatment regimen, e.g., pre-screening patients prior to vaccination to determine which of the peptides (SEQ ID NOS 1-45) are most suitable for a combination of peptides in the vaccine for a specific patient.

In addition to selecting the ideal TAA to target, strategies to optimize anti-tumor immunity incorporate approaches to prevent the escape of cancer cells from immune recognition. Mechanisms that underlie cancer cell escape, e.g., cell surface inhibitory molecules and immunoregulatory cells including $T_{reg}$ and myeloid-derived suppressor cells have been reported.[31-34] The findings demonstrated an enhanced T cell response to ASPH following CD25+ $T_{reg}$ cell depletion. Moreover, residual tumor cells still expressed cell surface ASPH in a mouse model following immunization with ASPH-loaded DCs implying the existence of tumor cells that escape immunotherapy.[12] Thus, a combination therapy strategy using ASPH-based immunotherapy in combination with other approaches (e.g., antagonizing $T_{reg}$ cell function) circumvent immune escape and achieve a successful clinical outcome.[35] Low doses of cyclophosphamide, for example, reportedly decrease the number and inhibitory activity of $T_{reg}$ cells by suppressing the expression of important functional markers: forkhead box P3 and glucocorticoid-induced TNF-receptor-related protein.[36] In a tumor-bearing mouse model, cyclophosphamide treatment suppressed $T_{reg}$ cell function and augmented the immune response and tumor eradication.[37] Similarly, sorafenib (a multi-targeted anti-angiogenic tyrosine kinase inhibitor used to treat patients with advanced HCC) reduced $T_{reg}$ cell function and enhanced anti-tumor immunity in mice bearing established orthotropic HCC.[38] Optionally, these agents are used as an adjunct therapy to the vaccine peptides.

Other treatment options such as transarterial embolization or local ablation therapy are useful to augment ASPH-based HCC immunotherapy. Transarterial embolization, for example, not only induced tumor necrosis directly, but also expanded the T cell-mediated immune response.[39] Radiofrequency HCC ablation induced peptide-specific CTLs.[40] ASPH-based immunotherapy can be combined with additional approaches to treat HCC and augment the possible clinical effect of peptide epitope based therapy.

The results indicate that $T_{reg}$ cells comprise a small component of the T cell population activated by the entire ASPH protein sequence. A major advantage of peptide-based, versus whole protein-based, vaccines is that $T_{reg}$ cell epitopes can readily be identified and omitted.

Figure 6:
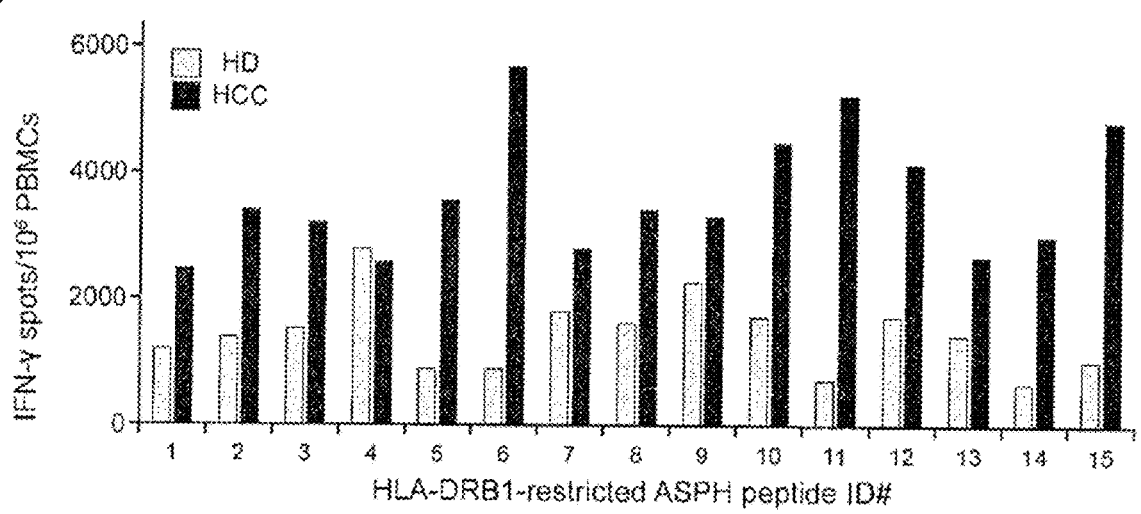
FIG. 6 is a bar graph. Summary and comparison of the responses of the healthy donors (HD) and HCC patients (HCC) to HLA-DRB1-restricted ASPH peptides. The responses (IFN-γ spots/106 PBMCs) of 5 healthy donors (#1-5) and 6 HCC patients (#7-12) to the 15 individual HLA-DRB1-restricted peptides down in FIGS. 2 and 4A, respectively, were combined and averaged; the background, DMSO control was subtracted.

The data reported herein demonstrated that ASPH elicits antigen-specific CD4+ T cell and CD8+ CTL activation, and that ASPH-derived HLA class I- and class II-restricted purified peptides activate CD4+ T cells and CD8+ CTLs derived from HCC patients. The average responses of the healthy donors and the HCC patients to the HLA-DRB1-restricted ASPH peptides (shown in FIG. 2 and FIG. 4A respectively) are summarized and compared in FIG. 6. In the case of healthy donors (HD) naïve T cells represent the vast majority of induced antigen-specific T-cell. However, in HCC patients it may be a combination of both naïve cells and previously sensitized cells. Considering the immunogenicity of ASPH, its tissue specificity and association with tumor progression, ASPH peptide-based vaccination represents an improved HCC treatment and treatment of other tumor types characterized by aberrant, e.g., overexpression of ASPH. Overexpression of ASPH refers to expression level of ASPH of the tissues or cells from a subject is 10%, 20%, 30%, 40%, 50%, 60%, 70%, 80%, 90%, 100%, 200% or more than the expression level of ASPH of the tissues or cells from a healthy subject or a subject without cancer.

TABLE I

Predicted, HLA-DRB1-restricted ASPH immunogenic consensus sequences

| Peptide ID# | Peptide name | AA position | AA sequence | SEQ ID NO |
|---|---|---|---|---|
| 1 | p52 | 52-71 | TSFFTWFMVIALLGVWTSVA | 1 |
| 2 | p103 | 103-117 | AKVLLGLKERSTSEP | 2 |
| 3 | p148 | 148-166 | KEQIQSLLHEMVHAEHVEG | 3 |
| 4 | p322 | 322-337 | QKAKVKKKKPKLLNKF | 4 |
| 5 | p415 | 415-432 | PADLLKLSLKRRSDRQQF | 5 |
| 6 | p427 | 427-444 | SDRQQFLGHMRGSLLTLQ | 6 |
| 7 | p437 | 437-452 | RGSLLTLQRLVQLFPN | 7 |
| 8 | p443 | 443-458 | LQRLVQLFPNDTSLKN | 8 |
| 9 | p492 | 492-509 | VHYGFILKAQNKIAESIP | 9 |
| 10 | p557 | 557-576 | ASVWQRSLYNVNGLKAQPWW | 10 |
| 11 | p581 | 581-597 | TGYTELVKSLERNWKLI | 11 |
| 12 | p588 | 588-607 | KSLERNWKLIRDEGLAVMDK | 12 |
| 13 | p725 | 725-738 | HEVWQDASSFRLIF | 13 |
| 14 | p731 | 731-747 | ASSFRLIFIVDVWHPEL | 14 |
| 15 | p740 | 740-758 | VDVWHPELTPQQRRSLPAI | 15 |

ASPH, aspartate-β-hydroxylase; AA, amino acid

TABLE II

Predicted, HLA class I-restricted ASPH peptide sequences

| Peptide ID# | Peptide name | AA position | AA sequence | Restricting HLA allele | SEQ ID NO |
|---|---|---|---|---|---|
| 1 | ASPH48 | 48-56 | GLSGTSFFT | A*0201 | 16 |
| 2 | ASPH53 | 53-61 | SFFTWFMVI | A*2402 | 17 |
| 3 | ASPH58 | 58-66 | FMVIALLGV | A*0201 | 18 |
| 4 | ASPH62 | 62-70 | ALLGVWTSV | A*0201 | 19 |
| 5 | ASPH72 | 72-80 | VVWFDLVDY | A*0101, A*0301, B*0702 | 20 |
| 6 | ASPH79 | 79-87 | DYEEVLGKL | A*2402 | 21 |
| 7 | ASPH81 | 81-89 | EEVLGKLGI | B*4403 | 22 |
| 8 | ASPH252 | 252-260 | TDDVTYQVY | A*0101, B*4403 | 23 |
| 9 | ASPH258 | 258-266 | QVYEEQAVY | A*0101, A0301 | 24 |
| 10 | ASPH261 | 261-269 | EEQAVYEPL | B*4403 | 25 |
| 11 | ASPH371 | 371-379 | YPQSPRARY | A*0101, B*0702 | 26 |
| 12 | ASPH374 | 374-382 | SPRARYGKA | B*0702 | 27 |
| 13 | ASPH406 | 406-414 | QEVASLPDV | B*4403 | 28 |
| 14 | ASPH411 | 411-419 | LPDVPADLL | B*0702 | 29 |
| 15 | ASPH475 | 475-483 | KVYEEVLSV | A*0201 | 30 |
| 16 | ASPH478 | 478-486 | EEVLSVTPN | B*4403 | 31 |
| 17 | ASPH484 | 484-492 | TPNDGFAKV | B*0702 | 32 |
| 18 | ASPH488 | 488-496 | GFAKVHYGF | A*2402 | 33 |
| 19 | ASPH491 | 491-499 | KVHYGFILK | A*0301 | 34 |
| 20 | ASPH503 | 503-511 | KIAESIPYL | A*0201 | 35 |
| 21 | ASPH521 | 521-529 | GTDDGRFYF | A*0101 | 36 |
| 22 | ASPH537 | 537-545 | RVGNKEAYK | A*0301 | 37 |
| 23 | ASPH557 | 557-565 | ASVWQRSLY | A*0101, A*0301, B*4403 | 38 |
| 24 | ASPH563 | 563-571 | SLYNVNGLK | A*0301 | 39 |
| 25 | ASPH582 | 582-590 | GYTELVKSL | A*2402 | 40 |
| 26 | ASPH611 | 611-619 | LFLPEDENL | A*2402 | 41 |
| 27 | ASPH681 | 681-689 | GPTNCRLRM | B*0702 | 42 |

TABLE II-continued

Predicted, HLA class I-restricted ASPH peptide sequences

| Peptide ID# | Peptide name | AA position | AA sequence | Restricting HLA allele | SEQ ID NO |
|---|---|---|---|---|---|
| 28 | ASPH693 | 693-701 | LVIPKEGCK | A*0301 | 43 |
| 29 | ASPH701 | 701-709 | KIRCANETR | A*0301 | 44 |
| 30 | ASPH711 | 711-719 | WEEGKVLIF | B*4403 | 45 |

ASPH, aspartate-β-hydroxylase; AA, amino acid

TABLE 3

HCC patient characteristics

| | HLA alleles | | | | Age | | | Maximum tumor size | | Risk |
|---|---|---|---|---|---|---|---|---|---|---|
| ID | A | B | C | DR | (years) | Gender | Histology | (cm) | Multiplicity | factor |
| HCC #1 | | ND | | | 67 | Male | W | 1.0 | Single | Alcohol |
| HCC #2 | | ND | | | 58 | Male | M | 5.5 | Multiple | HCV |
| HCC #3 | | ND | | | 84 | Male | W | 8.0 | Single | Alcohol |
| HCC #4 | | ND | | | 72 | Male | W | 15.0 | Multiple | None |
| HCC #5 | | ND | | | 53 | Male | W | 2.0 | Single | HCV |
| HCC #6 | *01/*03 | *07/*08 | *07/— | *02/*06 | 70 | Female | W | 8.0 | Single | HCV |
| HCC #7 | *01/*02 | *49/*53 | *04/*07 | *05/*06 | 82 | Male | ND | 6.5 | Single | None |
| HCC #8 | *25/*68 | *18/*35 | *04/*12 | *06/*07 | 69 | Male | ND | 4.8 | Single | None |
| HCC #9 | *02/*24 | *35/*53 | *04/— | *05/*06 | 57 | Male | ND | 1.6 | Single | None |
| HCC #10 | *02/*33 | *44/*65 | *04/*08 | *02/*09 | 64 | Female | M | 9.4 | Single | None |
| HCC #11 | *02/*29 | *51/— | *04/— | *05/*06 | 70 | Female | W | 5.8 | Multiple | HCV |
| HCC #12 | *03/*23 | *07/*44 | *04/*07 | *02/*05 | 70 | Male | M | 2.7 | Single | HCV |

ND, not determined:
W, well differentiated;
M, moderately differentiated;
HCV, hepatitis C virus

REFERENCES

1. El-Serag H B, Rudolph K L. Hepatocellular carcinoma: epidemiology and molecular carcinogenesis. Gastroenterology 2007; 132:2557-76.
2. Schutte K, Bornschein J, Malfertheiner P. Hepatocellular carcinoma—epidemiological trends and risk factors. Digestive diseases 2009; 27:80-92.
3. Fong Y, Sun R L, Jarnagin W, et al. An analysis of 412 cases of hepatocellular carcinoma at a Western center. Annals of surgery 1999; 229:790-9; discussion 799-800.
4. Zhu A X. Systemic therapy of advanced hepatocellular carcinoma: how hopeful should we be? The oncologist 2006; 11:790-800.
5. Jia S, VanDusen W J, Diehl R E, et al. cDNA cloning and expression of bovine aspartyl (asparaginyl) beta-hydroxylase. The Journal of biological chemistry 1992; 267:14322-7.
6. Lavaissiere L, Jia S, Nishiyama M, et al. Overexpression of human aspartyl(asparaginyl)beta-hydroxylase in hepatocellular carcinoma and cholangiocarcinoma. The Journal of clinical investigation 1996; 98:1313-23.
7. Gronke R S, VanDusen W J, Garsky V M, et al. Aspartyl beta-hydroxylase: in vitro hydroxylation of a synthetic peptide based on the structure of the first growth factor-like domain of human factor IX. Proceedings of the National Academy of Sciences of the United States of America 1989; 86:3609-13.
8. Gronke R S, Welsch D J, VanDusen W J, et al. Partial purification and characterization of bovine liver aspartyl beta-hydroxylase. The Journal of biological chemistry 1990; 265:8558-65.
9. de la Monte S M, Tamaki S, Cantarini M C, et al. Aspartyl-(asparaginyl)-beta-hydroxylase regulates hepatocellular carcinoma invasiveness. Journal of hepatology 2006; 44:971-83.
10. Wang K, Liu J, Yan Z L, et al. Overexpression of aspartyl-(asparaginyl)-beta-hydroxylase in hepatocellular carcinoma is associated with worse surgical outcome. Hepatology 2010; 52:164-73.
11. Shimoda M, Tomimaru Y, Charpentier K P, et al. Tumor progression-related transmembrane protein aspartate-beta-hydroxylase is a target for immunotherapy of hepatocellular carcinoma. Journal of hepatology 2012; 56:1129-35.
12. Noda T, Shimoda M, Ortiz V, et al. Immunization with aspartate-beta-hydroxylase-loaded dendritic cells produces antitumor effects in a rat model of intrahepatic cholangiocarcinoma. Hepatology 2012; 55:86-97.
13. De Groot A S, Jesdale B M, Szu E, et al. An interactive Web site providing major histocompatibility ligand predictions: application to HIV research. AIDS research and human retroviruses 1997; 13:529-31.
14. Schafer J R, Jesdale B M, George J A, et al. Prediction of well-conserved HIV-1 ligands using a matrix-based algorithm, EpiMatrix. Vaccine 1998; 16:1880-4.
15. Southwood S, Sidney J, Kondo A, et al. Several common HLA-DR types share largely overlapping peptide binding repertoires. Journal of immunology 1998; 160:3363-73.
16. De Groot A S, Bishop E A, Khan B, et al. Engineering immunogenic consensus T helper epitopes for a cross-clade HIV vaccine. Methods 2004; 34:476-87.
17. Sette A, Sidney J. Nine major HLA class I supertypes account for the vast preponderance of HLA-A and-B polymorphism. Immunogenetics 1999; 50:201-12.
18. Meyer T P, Zehnter I, Hofmann B, et al. Filter Buffy Coats (FBC): a source of peripheral blood leukocytes recovered from leukocyte depletion filters. J Immunol Methods 2005; 307:150-66.
19. Dannull J, Su Z, Rizzieri D, et al. Enhancement of vaccine-mediated antitumor immunity in cancer patients after depletion of regulatory T cells. The Journal of clinical investigation 2005; 115:3623-33.
20. Moser J M, Sassano E R, Leistritz del C, et al. Optimization of a dendritic cell-based assay for the in vitro priming of naive human CD4+ T cells. J Immunol Methods 2010; 353:8-19.
21. Mishra S, Losikoff P T, Self A A, et al. Peptide-pulsed dendritic cells induce the hepatitis C viral epitope-specific responses of naïve human T cells. Vaccine 2014; in press.
22. Frentsch M, Arbach O, Kirchhoff D, et al. Direct access to CD4+ T cells specific for defined antigens according to CD154 expression. Nature medicine 2005; 11:1118-24.
23. Wolfl M, Kuball J, Ho W Y, et al. Activation-induced expression of CD137 permits detection, isolation, and expansion of the full repertoire of CD8+ T cells responding to antigen without requiring knowledge of epitope specificities. Blood 2007; 110:201-10.
24. Kennedy R, Celis E. Multiple roles for CD4+ T cells in anti-tumor immune responses. Immunological reviews 2008; 222:129-44.
25. Marzo A L, Kinnear B F, Lake R A, et al. Tumor-specific CD4+ T cells have a major "post-licensing" role in CTL mediated anti-tumor immunity. Journal of immunology 2000; 165:6047-55.
26. Breous E, Thimme R. Potential of immunotherapy for hepatocellular carcinoma. Journal of hepatology 2011; 54:830-4.
27. Komori H, Nakatsura T, Senju S, et al. Identification of HLA-A2- or HLA-A24-restricted CTL epitopes possibly useful for glypican-3-specific immunotherapy of hepatocellular carcinoma. Clinical cancer research: an official journal of the American Association for Cancer Research 2006; 12:2689-97.
28. Liu Y, Daley S, Evdokimova V N, et al. Hierarchy of alpha fetoprotein (AFP)-specific T cell responses in subjects with AFP-positive hepatocellular cancer. Journal of immunology 2006; 177:712-21.
29. Shang X Y, Chen H S, Zhang H G, et al. The spontaneous CD8+ T-cell response to HLA-A2-restricted NY-ESO-1b peptide in hepatocellular carcinoma patients. Clinical cancer research: an official journal of the American Association for Cancer Research 2004; 10:6946-55.
30. Thimme R, Neagu M, Boettler T, et al. Comprehensive analysis of the alpha-fetoprotein-specific CD8+ T cell responses in patients with hepatocellular carcinoma. Hepatology 2008; 48:1821-33.
31. Zou W. Regulatory T cells, tumour immunity and immunotherapy. Nature reviews. Immunology 2006; 6:295-307.
32. Sakaguchi S. Naturally arising CD4+ regulatory t cells for immunologic self-tolerance and negative control of immune responses. Annual review of immunology 2004; 22:531-62.
33. Hoechst B, Ormandy L A, Ballmaier M, et al. A new population of myeloid-derived suppressor cells in hepatocellular carcinoma patients induces CD4(+)CD25(+) Foxp3(+) T cells. Gastroenterology 2008; 135:234-43.
34. Shi F, Shi M, Zeng Z, et al. PD-1 and PD-L1 upregulation promotes CD8(+) T-cell apoptosis and postoperative recurrence in hepatocellular carcinoma patients. International journal of cancer. Journal international du cancer 2011; 128:887-96.
35. Zitvogel L, Apetoh L, Ghiringhelli F, et al. Immunological aspects of cancer chemotherapy. Nature reviews. Immunology 2008; 8:59-73.
36. Lutsiak M E, Semnani R T, De Pascalis R, et al. Inhibition of CD4(+)25+ T regulatory cell function implicated in enhanced immune response by low-dose cyclophosphamide. Blood 2005; 105:2862-8.
37. Schiavoni G, Mattei F, Di Pucchio T, et al. Cyclophosphamide induces type I interferon and augments the number of CD44(hi) T lymphocytes in mice: implications for strategies of chemoimmunotherapy of cancer. Blood 2000; 95:2024-30.
38. Chen M L, Yan B S, Lu W C, et al. Sorafenib relieves cell-intrinsic and cell-extrinsic inhibitions of effector T cells in tumor microenvironment to augment antitumor immunity. Int J Cancer 2014; 134:319-31.
39. Ayaru L, Pereira S P, Alisa A, et al. Unmasking of alpha-fetoprotein-specific CD4(+) T cell responses in hepatocellular carcinoma patients undergoing embolization. Journal of immunology 2007; 178:1914-22.
40. Nobuoka D, Motomura Y, Shirakawa H, et al. Radiofrequency ablation for hepatocellular carcinoma induces glypican-3 peptide-specific cytotoxic T lymphocytes. Int J Oncol 2012; 40:63-70.

What is claimed:

1. A method for reducing growth of an aspartate-β-hydroxylase (ASPH)-expressing tumor in a subject, comprising
selecting a suitable ASPH peptide for said subject by contacting a subject-derived peripheral blood mononuclear cell (PBMC) or T cell with a purified ASPH peptide, wherein said ASPH peptide is selected from the group consisting of SEQ ID NOs: 1-45, and wherein a selected peptide is characterized as eliciting an ASPH-specific HLA class I- or class II-restricted T cell response; and
administering to the subject a therapeutically effective amount of a purified said selected peptide.

2. A method for preventing development of an aspartate-β-hydroxylase (ASPH)-expressing tumor in a subject, comprising
identifying a subject suffering from an ASPH-expressing tumor;
selecting a suitable ASPH peptide for said subject by contacting a subject-derived peripheral blood mononuclear cell (PBMC) or T cell with a purified ASPH peptide, wherein said ASPH peptide is selected from the group consisting of SEQ ID NOs: 1-45, and wherein a selected peptide is characterized as eliciting an ASPH-specific HLA class I- or class II-restricted T cell response; and
administering to said subject a therapeutically effective amount of a purified said selected peptide.

3. A method for reducing metastasis of an aspartate-β-hydroxylase (ASPH)-expressing tumor in a subject, comprising
selecting a suitable ASPH peptide for said subject by contacting a subject-derived peripheral blood mononuclear cell (PBMC) or T cell with a purified ASPH peptide, wherein said ASPH peptide is selected from the group consisting of SEQ ID NOs: 1-45, and wherein a selected peptide is characterized as eliciting an ASPH-specific HLA class I- or class II-restricted T cell response; and
administering to the subject a therapeutically effective amount of a purified said selected peptide.

4. The method of claim 1, wherein said tumor is selected from the group consisting of liver, gastrointestinal, pancreas, breast, prostate, cervix, ovary, fallopian tube, larynx, lung, thyroid, gall bladder, kidney, bladder, and brain cancers.

5. The method of claim 1, wherein said subject is a human, canine, feline, equine, bovine, or porcine subject.

6. The method of claim 1, further comprising a second therapy prior to, concurrently or subsequent to the administration step.

7. The method of claim 6, wherein the second therapy is trans-arterial embolization (TAE), trans-arterial chemoembolization (TACE), radioembolization (RE) and/or local ablation.

8. The method of claim 1, wherein said selected peptide elicits a HLA-DRB1-restricted ASPH T cell response.

9. The method of claim 8, wherein said T cell response is restricted to one or more of HLA-DRB1 alleles selected from the group consisting of DRB1*0101, DRB1*0301, DRB1*0401, DRB1*0701, DRB1*0801, DRB1*1101, DRB1*1301, and DRB1*1501.

10. The method of claim 1, wherein said selected peptide elicits an HLA-A or HLA-B restricted ASPH T cell response.

11. The method of claim 10, wherein said T cell response is restricted to one or more HLA-A alleles selected from the group consisting of A*0101, A*0201, A*0301, and A*2402.

12. The method of claim 10, wherein said T cell response is restricted to one or more HLA-B alleles selected from the group consisting of B*0702, and B*4403.

13. The method of claim 1, 2 or 3, wherein the ASPH peptide comprises the amino acid sequence of TGYTELVK-SLERNWKLI (SEQ ID NO:11).

14. The method of claim 13, wherein said method elicits an HLA class II restricted ASPH-specific immune response.

15. The method of claim 1, 2 or 3, wherein the ASPH peptide comprises the amino acid sequence of YPQSPRARY (SEQ ID NO:26).

16. The method of claim 15, wherein said method elicits an HLA class I restricted ASPH-specific immune response.

* * * * *

SEQUENCE LISTING

```
<160> NUMBER OF SEQ ID NOS: 47

<210> SEQ ID NO 1
<211> LENGTH: 20
<212> TYPE: PRT
<213> ORGANISM: Artificial Sequence
<220> FEATURE:
<223> OTHER INFORMATION: p52

<400> SEQUENCE: 1

Thr Ser Phe Phe Thr Trp Phe Met Val Ile Ala Leu Leu Gly Val Trp
1               5                   10                  15

Thr Ser Val Ala
            20

<210> SEQ ID NO 2
<211> LENGTH: 15
<212> TYPE: PRT
<213> ORGANISM: Artificial Sequence
<220> FEATURE:
```

```
<223> OTHER INFORMATION: p103

<400> SEQUENCE: 2

Ala Lys Val Leu Leu Gly Leu Lys Glu Arg Ser Thr Ser Glu Pro
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: p148

<400> SEQUENCE: 3

Lys Glu Gln Ile Gln Ser Leu Leu His Glu Met Val His Ala Glu His
1               5                   10                  15

Val Glu Gly

<210> SEQ ID NO 4
<211> LENGTH: 16
<212> TYPE: PRT
<213> ORGANISM: Artificial Sequence
<220> FEATURE:
<223> OTHER INFORMATION: p322

<400> SEQUENCE: 4

Gln Lys Ala Lys Val Lys Lys Lys Pro Lys Leu Leu Asn Lys Phe
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: p415

<400> SEQUENCE: 5

Pro Ala Asp Leu Leu Lys Leu Ser Leu Lys Arg Arg Ser Asp Arg Gln
1               5                   10                  15

Gln Phe

<210> SEQ ID NO 6
<211> LENGTH: 18
<212> TYPE: PRT
<213> ORGANISM: Artificial Sequence
<220> FEATURE:
<223> OTHER INFORMATION: p427

<400> SEQUENCE: 6

Ser Asp Arg Gln Gln Phe Leu Gly His Met Arg Gly Ser Leu Leu Thr
1               5                   10                  15

Leu Gln

<210> SEQ ID NO 7
<211> LENGTH: 16
<212> TYPE: PRT
<213> ORGANISM: Artificial Sequence
<220> FEATURE:
<223> OTHER INFORMATION: p437

<400> SEQUENCE: 7

Arg Gly Ser Leu Leu Thr Leu Gln Arg Leu Val Gln Leu Phe Pro Asn
1               5                   10                  15
```

```
<210> SEQ ID NO 8
<211> LENGTH: 16
<212> TYPE: PRT
<213> ORGANISM: Artificial Sequence
<220> FEATURE:
<223> OTHER INFORMATION: p443

<400> SEQUENCE: 8

Leu Gln Arg Leu Val Gln Leu Phe Pro Asn Asp Thr Ser Leu Lys Asn
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: p492

<400> SEQUENCE: 9

Val His Tyr Gly Phe Ile Leu Lys Ala Gln Asn Lys Ile Ala Glu Ser
1               5                   10                  15

Ile Pro

<210> SEQ ID NO 10
<211> LENGTH: 20
<212> TYPE: PRT
<213> ORGANISM: Artificial Sequence
<220> FEATURE:
<223> OTHER INFORMATION: p557

<400> SEQUENCE: 10

Ala Ser Val Trp Gln Arg Ser Leu Tyr Asn Val Asn Gly Leu Lys Ala
1               5                   10                  15

Gln Pro Trp Trp
            20

<210> SEQ ID NO 11
<211> LENGTH: 17
<212> TYPE: PRT
<213> ORGANISM: Artificial Sequence
<220> FEATURE:
<223> OTHER INFORMATION: p581

<400> SEQUENCE: 11

Thr Gly Tyr Thr Glu Leu Val Lys Ser Leu Glu Arg Asn Trp Lys Leu
1               5                   10                  15

Ile

<210> SEQ ID NO 12
<211> LENGTH: 20
<212> TYPE: PRT
<213> ORGANISM: Artificial Sequence
<220> FEATURE:
<223> OTHER INFORMATION: p588

<400> SEQUENCE: 12

Lys Ser Leu Glu Arg Asn Trp Lys Leu Ile Arg Asp Glu Gly Leu Ala
1               5                   10                  15

Val Met Asp Lys
            20

<210> SEQ ID NO 13
<211> LENGTH: 14
<212> TYPE: PRT
<213> ORGANISM: Artificial Sequence
```

<220> FEATURE:
<223> OTHER INFORMATION: p725

<400> SEQUENCE: 13

His Glu Val Trp Gln Asp Ala Ser Ser Phe Arg Leu Ile Phe
1               5                   10

<210> SEQ ID NO 14
<211> LENGTH: 17
<212> TYPE: PRT
<213> ORGANISM: Artificial Sequence
<220> FEATURE:
<223> OTHER INFORMATION: p731

<400> SEQUENCE: 14

Ala Ser Ser Phe Arg Leu Ile Phe Ile Val Asp Val Trp His Pro Glu
1               5                   10                  15

Leu

<210> SEQ ID NO 15
<211> LENGTH: 19
<212> TYPE: PRT
<213> ORGANISM: Artificial Sequence
<220> FEATURE:
<223> OTHER INFORMATION: VDVWHPELTPQQRRSLPAI

<400> SEQUENCE: 15

Val Asp Val Trp His Pro Glu Leu Thr Pro Gln Gln Arg Arg Ser Leu
1               5                   10                  15

Pro Ala Ile

<210> SEQ ID NO 16
<211> LENGTH: 9
<212> TYPE: PRT
<213> ORGANISM: Artificial Sequence
<220> FEATURE:
<223> OTHER INFORMATION: ASPH48

<400> SEQUENCE: 16

Gly Leu Ser Gly Thr Ser Phe Phe Thr
1               5

<210> SEQ ID NO 17
<211> LENGTH: 9
<212> TYPE: PRT
<213> ORGANISM: Artificial Sequence
<220> FEATURE:
<223> OTHER INFORMATION: ASPH53

<400> SEQUENCE: 17

Ser Phe Phe Thr Trp Phe Met Val Ile
1               5

<210> SEQ ID NO 18
<211> LENGTH: 9
<212> TYPE: PRT
<213> ORGANISM: Artificial Sequence
<220> FEATURE:
<223> OTHER INFORMATION: ASPH58

<400> SEQUENCE: 18

Phe Met Val Ile Ala Leu Leu Gly Val
1               5

<210> SEQ ID NO 19

```
<211> LENGTH: 9
<212> TYPE: PRT
<213> ORGANISM: Artificial Sequence
<220> FEATURE:
<223> OTHER INFORMATION: ASPH62

<400> SEQUENCE: 19

Ala Leu Leu Gly Val Trp Thr Ser Val
1               5

<210> SEQ ID NO 20
<211> LENGTH: 9
<212> TYPE: PRT
<213> ORGANISM: Artificial Sequence
<220> FEATURE:
<223> OTHER INFORMATION: ASPH72

<400> SEQUENCE: 20

Val Val Trp Phe Asp Leu Val Asp Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: ASPH79

<400> SEQUENCE: 21

Asp Tyr Glu Glu Val Leu Gly Lys Leu
1               5

<210> SEQ ID NO 22
<211> LENGTH: 9
<212> TYPE: PRT
<213> ORGANISM: Artificial Sequence
<220> FEATURE:
<223> OTHER INFORMATION: ASPH81

<400> SEQUENCE: 22

Glu Glu Val Leu Gly Lys Leu Gly Ile
1               5

<210> SEQ ID NO 23
<211> LENGTH: 9
<212> TYPE: PRT
<213> ORGANISM: Artificial Sequence
<220> FEATURE:
<223> OTHER INFORMATION: ASPH252

<400> SEQUENCE: 23

Thr Asp Asp Val Thr Tyr Gln Val Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: ASPH258

<400> SEQUENCE: 24

Gln Val Tyr Glu Glu Gln Ala Val Tyr
1               5

<210> SEQ ID NO 25
<211> LENGTH: 9
```

```
<212> TYPE: PRT
<213> ORGANISM: Artificial Sequence
<220> FEATURE:
<223> OTHER INFORMATION: ASPH261

<400> SEQUENCE: 25

Glu Glu Gln Ala Val Tyr Glu Pro Leu
1               5

<210> SEQ ID NO 26
<211> LENGTH: 9
<212> TYPE: PRT
<213> ORGANISM: Artificial Sequence
<220> FEATURE:
<223> OTHER INFORMATION: ASPH371

<400> SEQUENCE: 26

Tyr Pro Gln Ser Pro Arg Ala Arg Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: ASPH374

<400> SEQUENCE: 27

Ser Pro Arg Ala Arg Tyr Gly Lys Ala
1               5

<210> SEQ ID NO 28
<211> LENGTH: 9
<212> TYPE: PRT
<213> ORGANISM: Artificial Sequence
<220> FEATURE:
<223> OTHER INFORMATION: ASPH406

<400> SEQUENCE: 28

Gln Glu Val Ala Ser Leu Pro Asp Val
1               5

<210> SEQ ID NO 29
<211> LENGTH: 9
<212> TYPE: PRT
<213> ORGANISM: Artificial Sequence
<220> FEATURE:
<223> OTHER INFORMATION: ASPH411

<400> SEQUENCE: 29

Leu Pro Asp Val Pro Ala Asp Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: ASPH475

<400> SEQUENCE: 30

Lys Val Tyr Glu Glu Val Leu Ser Val
1               5

<210> SEQ ID NO 31
<211> LENGTH: 9
<212> TYPE: PRT
```

```
<213> ORGANISM: Artificial Sequence
<220> FEATURE:
<223> OTHER INFORMATION: ASPH478

<400> SEQUENCE: 31

Glu Glu Val Leu Ser Val Thr Pro Asn
1               5

<210> SEQ ID NO 32
<211> LENGTH: 9
<212> TYPE: PRT
<213> ORGANISM: Artificial Sequence
<220> FEATURE:
<223> OTHER INFORMATION: ASPH484

<400> SEQUENCE: 32

Thr Pro Asn Asp Gly Phe Ala Lys Val
1               5

<210> SEQ ID NO 33
<211> LENGTH: 9
<212> TYPE: PRT
<213> ORGANISM: Artificial Sequence
<220> FEATURE:
<223> OTHER INFORMATION: ASPH488

<400> SEQUENCE: 33

Gly Phe Ala Lys Val His Tyr Gly Phe
1               5

<210> SEQ ID NO 34
<211> LENGTH: 9
<212> TYPE: PRT
<213> ORGANISM: Artificial Sequence
<220> FEATURE:
<223> OTHER INFORMATION: ASPH491

<400> SEQUENCE: 34

Lys Val His Tyr Gly Phe Ile Leu Lys
1               5

<210> SEQ ID NO 35
<211> LENGTH: 9
<212> TYPE: PRT
<213> ORGANISM: Artificial Sequence
<220> FEATURE:
<223> OTHER INFORMATION: ASPH503

<400> SEQUENCE: 35

Lys Ile Ala Glu Ser Ile Pro Tyr Leu
1               5

<210> SEQ ID NO 36
<211> LENGTH: 9
<212> TYPE: PRT
<213> ORGANISM: Artificial Sequence
<220> FEATURE:
<223> OTHER INFORMATION: ASPH521

<400> SEQUENCE: 36

Gly Thr Asp Asp Gly Arg Phe Tyr Phe
1               5

<210> SEQ ID NO 37
<211> LENGTH: 9
<212> TYPE: PRT
<213> ORGANISM: Artificial Sequence
```

```
<220> FEATURE:
<223> OTHER INFORMATION: ASPH537

<400> SEQUENCE: 37

Arg Val Gly Asn Lys Glu Ala Tyr Lys
1               5

<210> SEQ ID NO 38
<211> LENGTH: 9
<212> TYPE: PRT
<213> ORGANISM: Artificial Sequence
<220> FEATURE:
<223> OTHER INFORMATION: ASPH557

<400> SEQUENCE: 38

Ala Ser Val Trp Gln Arg Ser Leu Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: ASPH563

<400> SEQUENCE: 39

Ser Leu Tyr Asn Val Asn Gly Leu Lys
1               5

<210> SEQ ID NO 40
<211> LENGTH: 9
<212> TYPE: PRT
<213> ORGANISM: Artificial Sequence
<220> FEATURE:
<223> OTHER INFORMATION: ASPH582

<400> SEQUENCE: 40

Gly Tyr Thr Glu Leu Val Lys Ser Leu
1               5

<210> SEQ ID NO 41
<211> LENGTH: 9
<212> TYPE: PRT
<213> ORGANISM: Artificial Sequence
<220> FEATURE:
<223> OTHER INFORMATION: ASPH611

<400> SEQUENCE: 41

Leu Phe Leu Pro Glu Asp Glu Asn Leu
1               5

<210> SEQ ID NO 42
<211> LENGTH: 9
<212> TYPE: PRT
<213> ORGANISM: Artificial Sequence
<220> FEATURE:
<223> OTHER INFORMATION: ASPH681

<400> SEQUENCE: 42

Gly Pro Thr Asn Cys Arg Leu Arg Met
1               5

<210> SEQ ID NO 43
<211> LENGTH: 9
<212> TYPE: PRT
<213> ORGANISM: Artificial Sequence
<220> FEATURE:
```

```
<223> OTHER INFORMATION: ASPH693

<400> SEQUENCE: 43

Leu Val Ile Pro Lys Glu Gly Cys Lys
1               5

<210> SEQ ID NO 44
<211> LENGTH: 9
<212> TYPE: PRT
<213> ORGANISM: Artificial Sequence
<220> FEATURE:
<223> OTHER INFORMATION: ASPH701

<400> SEQUENCE: 44

Lys Ile Arg Cys Ala Asn Glu Thr Arg
1               5

<210> SEQ ID NO 45
<211> LENGTH: 9
<212> TYPE: PRT
<213> ORGANISM: Artificial Sequence
<220> FEATURE:
<223> OTHER INFORMATION: ASPH711

<400> SEQUENCE: 45

Trp Glu Glu Gly Lys Val Leu Ile Phe
1               5

<210> SEQ ID NO 46
<211> LENGTH: 758
<212> TYPE: PRT
<213> ORGANISM: Homo sapiens

<400> SEQUENCE: 46

Met Ala Gln Arg Lys Asn Ala Lys Ser Ser Gly Asn Ser Ser Ser Ser
1               5                   10                  15

Gly Ser Gly Ser Gly Ser Thr Ser Ala Gly Ser Ser Ser Pro Gly Ala
                20                  25                  30

Arg Arg Glu Thr Lys His Gly Gly His Lys Asn Gly Arg Lys Gly Gly
            35                  40                  45

Leu Ser Gly Thr Ser Phe Phe Thr Trp Phe Met Val Ile Ala Leu Leu
        50                  55                  60

Gly Val Trp Thr Ser Val Ala Val Val Trp Phe Asp Leu Val Asp Tyr
65                  70                  75                  80

Glu Glu Val Leu Gly Lys Leu Gly Ile Tyr Asp Ala Asp Gly Asp Gly
                85                  90                  95

Asp Phe Asp Val Asp Asp Ala Lys Val Leu Leu Gly Leu Lys Glu Arg
            100                 105                 110

Ser Thr Ser Glu Pro Ala Val Pro Pro Glu Glu Ala Glu Pro His Thr
        115                 120                 125

Glu Pro Glu Glu Gln Val Pro Val Glu Ala Glu Pro Gln Asn Ile Glu
    130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
                165                 170                 175

Gly Glu Pro Gln Gln Glu Asp Asp Glu Phe Leu Met Ala Thr Asp Val
            180                 185                 190

Asp Asp Arg Phe Glu Thr Leu Glu Pro Glu Val Ser His Glu Glu Thr
        195                 200                 205
```

```
Glu His Ser Tyr His Val Glu Thr Val Ser Gln Asp Cys Asn Gln
    210                 215                 220

Asp Met Glu Glu Met Met Ser Glu Gln Glu Asn Pro Asp Ser Ser Glu
225                 230                 235                 240

Pro Val Val Glu Asp Glu Arg Leu His His Asp Thr Asp Asp Val Thr
                245                 250                 255

Tyr Gln Val Tyr Glu Glu Gln Ala Val Tyr Glu Pro Leu Glu Asn Glu
            260                 265                 270

Gly Ile Glu Ile Thr Glu Val Thr Ala Pro Pro Glu Asp Asn Pro Val
        275                 280                 285

Glu Asp Ser Gln Val Ile Val Glu Glu Val Ser Ile Phe Pro Val Glu
    290                 295                 300

Glu Gln Gln Glu Val Pro Pro Glu Thr Asn Arg Lys Thr Asp Asp Pro
305                 310                 315                 320

Glu Gln Lys Ala Lys Val Lys Lys Lys Pro Lys Leu Leu Asn Lys
                325                 330                 335

Phe Asp Lys Thr Ile Lys Ala Glu Leu Asp Ala Ala Glu Lys Leu Arg
                340                 345                 350

Lys Arg Gly Lys Ile Glu Glu Ala Val Asn Ala Phe Lys Glu Leu Val
            355                 360                 365

Arg Lys Tyr Pro Gln Ser Pro Arg Ala Arg Tyr Gly Lys Ala Gln Cys
370                 375                 380

Glu Asp Asp Leu Ala Glu Lys Arg Arg Ser Asn Glu Val Leu Arg Gly
385                 390                 395                 400

Ala Ile Glu Thr Tyr Gln Glu Val Ala Ser Leu Pro Asp Val Pro Ala
                405                 410                 415

Asp Leu Leu Lys Leu Ser Leu Lys Arg Arg Ser Asp Arg Gln Gln Phe
                420                 425                 430

Leu Gly His Met Arg Gly Ser Leu Leu Thr Leu Gln Arg Leu Val Gln
            435                 440                 445

Leu Phe Pro Asn Asp Thr Ser Leu Lys Asn Asp Leu Gly Val Gly Tyr
        450                 455                 460

Leu Leu Ile Gly Asp Asn Asp Asn Ala Lys Lys Val Tyr Glu Glu Val
465                 470                 475                 480

Leu Ser Val Thr Pro Asn Asp Gly Phe Ala Lys Val His Tyr Gly Phe
                485                 490                 495

Ile Leu Lys Ala Gln Asn Lys Ile Ala Glu Ser Ile Pro Tyr Leu Lys
                500                 505                 510

Glu Gly Ile Glu Ser Gly Asp Pro Gly Thr Asp Gly Arg Phe Tyr
            515                 520                 525

Phe His Leu Gly Asp Ala Met Gln Arg Val Gly Asn Lys Glu Ala Tyr
        530                 535                 540

Lys Trp Tyr Glu Leu Gly His Lys Arg Gly His Phe Ala Ser Val Trp
545                 550                 555                 560

Gln Arg Ser Leu Tyr Asn Val Asn Gly Leu Lys Ala Gln Pro Trp Trp
                565                 570                 575

Thr Pro Lys Glu Thr Gly Tyr Thr Glu Leu Val Lys Ser Leu Glu Arg
            580                 585                 590

Asn Trp Lys Leu Ile Arg Asp Glu Gly Leu Ala Val Met Asp Lys Ala
        595                 600                 605

Lys Gly Leu Phe Leu Pro Glu Asp Glu Asn Leu Arg Glu Lys Gly Asp
610                 615                 620
```

-continued

```
Trp Ser Gln Phe Thr Leu Trp Gln Gln Gly Arg Asn Glu Asn Ala
625                 630                 635                 640

Cys Lys Gly Ala Pro Lys Thr Cys Thr Leu Leu Glu Lys Phe Pro Glu
                645                 650                 655

Thr Thr Gly Cys Arg Arg Gly Gln Ile Lys Tyr Ser Ile Met His Pro
            660                 665                 670

Gly Thr His Val Trp Pro His Thr Gly Pro Thr Asn Cys Arg Leu Arg
        675                 680                 685

Met His Leu Gly Leu Val Ile Pro Lys Glu Gly Cys Lys Ile Arg Cys
    690                 695                 700

Ala Asn Glu Thr Arg Thr Trp Glu Glu Gly Lys Val Leu Ile Phe Asp
705                 710                 715                 720

Asp Ser Phe Glu His Glu Val Trp Gln Asp Ala Ser Ser Phe Arg Leu
                725                 730                 735

Ile Phe Ile Val Asp Val Trp His Pro Glu Leu Thr Pro Gln Gln Arg
            740                 745                 750

Arg Ser Leu Pro Ala Ile
        755
```

<210> SEQ ID NO 47
<211> LENGTH: 2324
<212> TYPE: DNA
<213> ORGANISM: Homo sapiens

<400> SEQUENCE: 47

| | | | | |
|---|---|---|---|---|
| cggaccgtgc | aatggcccag | cgtaagaatg | ccaagagcag | cggcaacagc agcagcagcg | 60 |
| gctccggcag | cggtagcacg | agtgcgggca | gcagcagccc | cggggcccgg agagagacaa | 120 |
| agcatggagg | acacaagaat | gggaggaaag | gcggactctc | gggaacttca ttcttcacgt | 180 |
| ggtttatggt | gattgcattg | ctgggcgtct | ggacatctgt | agctgtcgtt tggtttgatc | 240 |
| ttgttgacta | tgaggaagtt | ctaggaaaac | taggaatcta | tgatgctgat ggtgatggag | 300 |
| attttgatgt | ggatgatgcc | aaagttttat | taggacttaa | agagagatct acttcagagc | 360 |
| cagcagtccc | gccagaagag | gctgagccac | acactgagcc | cgaggagcag gttcctgtgg | 420 |
| aggcagaacc | ccagaatatc | gaagatgaag | caaaagaaca | aattcagtcc cttctccatg | 480 |
| aaatggtaca | cgcagaacat | gttgagggag | aagacttgca | acaagaagat ggacccacag | 540 |
| gagaaccaca | caagaggat | gatgagtttc | ttatggcgac | tgatgtagat gatagatttg | 600 |
| agaccctgga | acctgaagta | tctcatgaag | aaaccgagca | tagttaccac gtggaagaga | 660 |
| cagtttcaca | agactgtaat | caggatatgg | aagagatgat | gtctgagcag gaaaatccag | 720 |
| attccagtga | accagtagta | gaagatgaaa | gattgcacca | tgatacagat gatgtaacat | 780 |
| accaagtcta | tgaggaacaa | gcagtatatg | aacctctaga | aaatgaaggg atagaaatca | 840 |
| cagaagtaac | tgctcccccct | gaggataatc | ctgtagaaga | ttcacaggta attgtagaag | 900 |
| aagtaagcat | ttttcctgtg | gaaaacagc | aggaagtacc | accagaaaca aatagaaaaa | 960 |
| cagatgatcc | agaacaaaaa | gcaaaagtta | agaaaaagaa | gcctaaactt ttaaataaat | 1020 |
| ttgataagac | tattaaagct | gaacttgatg | ctgcagaaaa | actccgtaaa aggggaaaaa | 1080 |
| ttgaggaagc | agtgaatgca | tttaaagaac | tagtacgcaa | ataccctcag agtccacgag | 1140 |
| caagatatgg | gaaggcgcag | tgtgaggatg | atttggctga | agaggaga agtaatgagg | 1200 |
| tgctacgtgg | agccatcgag | acctaccaag | aggtggccag | cctacctgat gtccctgcag | 1260 |
| acctgctgaa | gctgagtttg | aagcgtcgct | cagacaggca | acaatttcta ggtcatatga | 1320 |

```
gaggttccct gcttaccctg cagagattag ttcaactatt tcccaatgat acttccttaa    1380
aaaatgacct tggcgtggga tacctcttga taggagataa tgacaatgca aagaaagttt    1440
atgaagaggt gctgagtgtg acacctaatg atggctttgc taaagtccat tatggcttca    1500
tcctgaaggc acagaacaaa attgctgaga gcatcccata tttaaaggaa ggaatagaat    1560
ccggagatcc tggcactgat gatgggagat tttatttcca cctgggggat gccatgcaga    1620
gggttgggaa caaagaggca tataagtggt atgagcttgg gcacaagaga ggacactttg    1680
catctgtctg gcaacgctca ctctacaatg tgaatggact gaaagcacag ccttggtgga    1740
ccccaaaaga aacgggctac acagagttag taaagtcttt agaaagaaac tggaagttaa    1800
tccgagatga aggccttgca gtgatggata aagccaaagg tctcttcctg cctgaggatg    1860
aaaacctgag ggaaaaaggg gactggagcc agttcacgct gtggcagcaa ggaagaagaa    1920
atgaaaatgc ctgcaaagga gctcctaaaa cctgtacctt actagaaaag ttccccgaga    1980
caacaggatg cagaagagga cagatcaaat attccatcat gcaccccggg actcacgtgt    2040
ggccgcacac agggcccaca aactgcaggc tccgaatgca cctgggcttg gtgattccca    2100
aggaaggctg caagattcga tgtgccaacg agaccaggac ctgggaggaa ggcaaggtgc    2160
tcatctttga tgactccttt gagcacgagg tatggcagga tgcctcatct ttccggctga    2220
tattcatcgt ggatgtgtgg catccggaac tgacaccaca gcagagacgc agccttccag    2280
caatttagca tgaattcatg caagcttggg aaactctgga gaga                    2324
```